(12) United States Patent
Somleva et al.

(10) Patent No.: US 8,487,159 B2
(45) Date of Patent: *Jul. 16, 2013

(54) PRODUCTION OF POLYHYDROXYBUTYRATE IN SWITCHGRASS

(75) Inventors: Mariya N. Somleva, Cambridge, MA (US); Kristi D. Snell, Belmont, MA (US); Julie Beaulieu, Cambridge, MA (US); Oliver P. Peoples, Arlington, MA (US); Bradley Garrison, Fulton, MD (US); Nii Patterson, Chelmsford, MA (US)

(73) Assignee: Metabolix, Inc., Cambridge, MA (US)

(*) Notice: Subject to any disclaimer, the term of this patent is extended or adjusted under 35 U.S.C. 154(b) by 847 days.

This patent is subject to a terminal disclaimer.

(21) Appl. No.: 12/431,428

(22) Filed: Apr. 28, 2009

(65) Prior Publication Data

US 2009/0271889 A1    Oct. 29, 2009

Related U.S. Application Data

(60) Provisional application No. 61/048,436, filed on Apr. 28, 2008.

(51) Int. Cl.
*C12N 15/09* (2006.01)
*C12N 15/31* (2006.01)
*C12N 15/82* (2006.01)
*A01H 5/00* (2006.01)
*A01H 5/10* (2006.01)

(52) U.S. Cl.
USPC ........... 800/288; 800/281; 800/284; 800/298; 435/419; 435/430

(58) Field of Classification Search
USPC ......................................... 800/281, 284, 288
See application file for complete search history.

(56) References Cited

U.S. PATENT DOCUMENTS

| | | | |
|---|---|---|---|
| 4,940,935 A | 7/1990 | Riley | |
| 4,945,050 A | 7/1990 | Sanford et al. | |
| 5,023,179 A | 6/1991 | Lam et al. | |
| 5,110,732 A | 5/1992 | Benfey et al. | |
| 5,188,642 A | 2/1993 | Shah et al. | |
| 5,240,855 A | 8/1993 | Tomes | |
| 5,268,463 A | 12/1993 | Jefferson | |
| 5,322,783 A | 6/1994 | Tomes et al. | |
| 5,324,646 A | 6/1994 | Buising et al. | |
| 5,380,831 A | 1/1995 | Adang et al. | |
| 5,399,680 A | 3/1995 | Zhu et al. | |
| 5,401,836 A | 3/1995 | Baszcynski et al. | |
| 5,451,513 A | 9/1995 | Maliga et al. | |
| 5,459,252 A | 10/1995 | Conkling et al. | |
| 5,466,785 A | 11/1995 | De Framond | |
| 5,534,432 A | 7/1996 | Peoples et al. | |
| 5,545,817 A | 8/1996 | McBride et al. | |
| 5,545,818 A | 8/1996 | McBride et al. | |
| 5,563,055 A | 10/1996 | Townsend et al. | |
| 5,569,597 A | 10/1996 | Grimsley et al. | |
| 5,593,874 A | 1/1997 | Brown et al. | |
| 5,604,121 A | 2/1997 | Hilder et al. | |
| 5,608,142 A | 3/1997 | Barton et al. | |
| 5,608,144 A | 3/1997 | Baden et al. | |
| 5,633,363 A | 5/1997 | Colbert et al. | |
| 5,639,949 A | 6/1997 | Ligon et al. | |
| 5,659,026 A | 8/1997 | Baszcynski et al. | |
| 5,663,063 A | 9/1997 | Peoples et al. | |
| 5,736,369 A | 4/1998 | Bowen et al. | |
| 5,750,386 A | 5/1998 | Conkling et al. | |
| 5,767,378 A | 6/1998 | Bojsen et al. | |
| 5,789,156 A | 8/1998 | Bujard et al. | |
| 5,814,618 A | 9/1998 | Bujard et al. | |
| 5,837,876 A | 11/1998 | Conkling et al. | |
| 6,072,050 A | 6/2000 | Bowen et al. | |
| 6,316,262 B1 | 11/2001 | Huisman et al. | |
| 6,448,473 B1 | 9/2002 | Mitsky et al. | |
| 7,732,680 B2 * | 6/2010 | Kourtz et al. | ................. 800/320 |

FOREIGN PATENT DOCUMENTS

| | | |
|---|---|---|
| WO | WO 95/16783 | 6/1995 |
| WO | WO 98/32326 | 7/1998 |
| WO | WO 99/43838 | 9/1999 |

OTHER PUBLICATIONS

Saruul, P. et al. Crop Sci. (2002) vol. 42: pp. 919-927.*
Arai et al., "Plastid Targeting of Polyhydroxybutyrate Biosynthetic Pathway in Tobacco", *Plant Biotechnol.*, 18(4):289-293 (2001).
Arai, et al., "Production of polyhydroxybutyrate by polycistronic expression of bacterial genes in tobacco plastid", *Plant Cell Physiol.*, 45(9):1176-84 (2004).
Bevan et al., "Structure and transcription of the nopaline synthase gene region of T-DNA", *Nucleic Acids Res.*, 11:369-385 (1983).
Bieles, "US facility brews up crop-based polymers", *Plastics and Rubber Weekly*, 17:1 (2006).
Blochinger and Diggelmann, "Hygromycin B phosphotransferase as a selectable marker for DNA transfer experiments with higher eukaryotic cells", *Mol. Cell. Biol.*, 4:2929-2931 (1984).
Bohmert et al., "Metabolic Engineering: Plastids as Bioreactors", *Molecular Biology and Biotechnology of Plant Organelles*, (Daniell and Chase, eds.), Kluwer Academic Publishers: Netherlands, 559-585 (2004).
Bohmert, et al., "Constitutive expression of the β-Ketothiolase gene in transgenic plants. A major obstacle for obtaining polyhydroxybutyrate-producing plants", *Plant Physiol.*, 128:1282-1290 (2002).
Bohmert, et al., "Transgenic *Arabidopsis* plants can accumulate polyhydroxybutyrate to up to 4% of their fresh weight", *Planta*, 211:841-845 (2000).
Bouton, "Molecular breeding of switchgrass for use as a biofuel crop", *Current Opinion in Genetics & Development*, 17(6):553-558 (2007).

(Continued)

*Primary Examiner* — Russell Kallis
(74) *Attorney, Agent, or Firm* — Pabst Patent Group LLP

(57) ABSTRACT

Transgenic plants, plant material, and plant cells for synthesis of polyhydroxyalkanoates, preferably poly(3-hydroxybutyrate) (also referred to a as PHB) are provided. Preferred plants that can be genetically engineered to produce PHB include plants that do not normally produce storage products such as oils and carbohydrates, and plants that have a $C_4$ NAD-malic enzyme photosynthetic pathway. Such plants also advantageously produce lignocellulosic biomass that can be converted into biofuels. An exemplary plant that can be genetically engineered to produce PHB and produce lignocellulosic biomass is switchgrass, *Panicum virgatum* L. A preferred cultivar of switchgrass is Alamo. Other suitable cultivars of switchgrass include but are not limited to Blackwell, Kanlow, Nebraska 28, Pathfinder, Cave-in-Rock, Shelter and Trailblazer.

15 Claims, 6 Drawing Sheets

OTHER PUBLICATIONS

Bytebier, et al., "T-DNA organization in tumor cultures and transgenic plants of the monocotyledon *Asparagus officinalis*" *Proc. Natl. Acad. Sci. USA*, 84:5345-5349 (1987).

Canevascini, et al., "Tissue-specific expression and promoter analysis of the tobacco ltp1 gene", *Plant Physiol.*, 112(2):513-524 (1996).

Cashmore, *Genetic Engineering of Plants*, (Kosuge, et al., eds.), Plenum Press: New York, 29-38 (1983).

Christou and Ford, "Parameters influencing stable transformation of rice immature embryos and recovery of transgenic plants using electric discharge particle acceleration", *Annals of Botany*, 75(4):407-413 (1995).

Christou, et al., "Stable transformation of soybean callus by DNA-coated gold particles", *Plant Physiol.*, 87:671-674 (1988).

Clark, et al., "Mutations at the transit peptide-mature protein junction separate two cleavage events during chloroplast import of the chlorophyll a/b-binding protein", *J. Biol. Chem.*, 264(29):17544-17550 (1989).

D'Halluin, et al., "Transgenic maize plants by tissue electroporation", *Plant Cell*, 4(12):1495-1505 (1992).

De Wet, et al., "Firefly luciferase gene: structure and expression in mammalian cells", *Mol. Cell. Biol.*, 7(2):725-737 (1987).

Della-Cioppa, et al., "Protein Trafficking in Plant Cells", *Plant Physiol.*, 84(4):965-968 (1987).

Denchev, et al., "Plant Regeneration from Callus Cultures of Switchgrass", *Crop Sci.*, 34:1623-1627 (1994).

Fromm, et al., "Inheritance and expression of chimeric genes in the progeny of transgenic maize plants", *Biotechnology (NY).*, 8(9):833-839 (1990).

Goff, et al., "Transactivation of anthocyanin biosynthetic genes following transfer of B regulatory genes into maize tissues", *EMBO J.*, 9(8):2517-2522 (1990).

Goldschmidt-Clermont, "Transgenic expression of aminoglycoside adenine transferase in the chloroplast: a selectable marker of site-directed transformation of chlamydomonas", *Nucl. Acids Res.*, 19(15):4083-4089 (1991).

Gotor, et al., "Analysis of three tissue-specific elements from the wheat Cab-1 enhancer", *Plant J*, 3(4):509-18 (2002).

Guevara-Garcia, et al., "Tissue-specific and wound-inducible pattern of expression of the mannopine synthase promoter is determined by the interaction between positive and negative cis-regulatory elements", *Plant J.*, 4(3):495-505 (1993).

Herrera, "Bonkers about biofuels", *Nature Biotechnol.* 24(7):755-760 (2006).

Houmiel, et al., "Poly(beta-hydroxybutyrate) production in oilseed leukoplasts of *Brassica napus*", *Planta*, 209(4):547-550 (1999).

John, et al., "Metabolic pathway engineering in cotton: biosynthesis of polyhydroxybutyrate in fiber cells", *Proc. Natl. Acad. Sci. USA*, 93(23):12768-12773 (1996).

Keller and Baumgartner, "Vascular-specific expression of the bean GRP 1.8 gene is negatively regulated", *Plant Cell*, 3(10):1051-1061 (1991).

Klein, et al., "Transfer of foreign genes into intact maize cells with high-velocity microprojectiles", *Proc. Natl. Acad. Sci. USA*, 85(12):4305-4309 (1988).

Klein, et al., "Genetic Transformation of Maize Cells by Particle Bombardment", *Plant Physiol.*, 91:440-444 (1989).

Kourtz, et al., "A novel thiolase-reductase gene fusion promotes the production of polyhydroxybutyrate in *Arabidopsis*", *Plant Biotechnol.*, 3(4):435-447 (2005).

Kourtz, et al., "Chemically inducible expression of the PHB biosynthetic pathway in *Arabidopsis*", *Transgenic Res.*, 16(6):759-769 (2007).

Kwon, et al., "Identification of a light-responsive region of the nuclear gene encoding the B subunit of chloroplast glyceraldehyde 3-phosphate dehydrogenase from *Arabidopsis thaliana*", *Plant Physiol.*, 105(1):357-67 (1994).

Lamppa, et al., "The chlorophyll a/b-binding protein inserts into the thylakoids independent of its cognate transit peptide", *J. Biol. Chem.*, 263(29):14996-14999 (1988).

Lawrence, et al., "Alterations in the *Chlamydomonas plastocyanin* transit peptide have distinct effects on in vitro import and in vivo protein accumulation", *J. Biol. Chem.*, 272(33):20357-20363 (1997).

Lössl, et al., "Inducible Trans-activation of Plastid Transgenes: Expression of the R. eutropha phb Operon in Transplastomic Tobacco", *Plant Cell Physiol.*, 46(9):1462-1471 (2005).

Lössl, et al., "Polyester synthesis in transplastomic tobacco (*Nicotiana tabacum* L.): significant contents of polyhydroxybutyrate are associated with growth reduction", *Plant Cell Rep.*, 21(9):891-899 (2003).

Madison and Huisman, "Metabolic engineering of poly(3-hydroxyalkanoates): from DNA to plastic", *Microbiol. Mol. Biol. Rev.*, 63(1):21-53 (1999).

Matsuoka, et al., "Tissue-specific light-regulated expression directed by the promoter of a C4 gene, maize pyruvate, orthophosphate dikinase, in a C3 plant, rice", *Proc. Natl. Acad. Sci. USA*, 90(20):9586-9590 (1993).

McBride et al., "Controlled expression of plastid transgenes in plants based on a nuclear DNA-encoded and plastid-targeted T7 RNA polymerase", *Proc. Natl. Acad. Sci. USA*, 91(15):7301-7305 (1994).

McElroy, et al., "Isolation of an efficient actin promoter for use in rice transformation", *Plant Cell*, 2(2):163-171 (1990).

McNellis, et al., "Glucocorticoid-inducible expression of a bacterial avirulence gene in transgenic *Arabidopsis* induces hypersensitive cell death", *Plant J.*, 14(2):247-257 (1998).

Menzel, et al., "Expression of bacterial poly(3-hydroxybutyrate) synthesis genes in hairy roots of sugar beet (*Beta vulgaris* L.)", *Appl Microbiol Biotechnol.* 60(5):571-6 (2003). Epub Oct. 24, 2002.

Miao, et al., "Ammonia-regulated expression of a soybean gene encoding cytosolic glutamine synthetase in transgenic *Lotus corniculatus*", *Plant Cell*, 3(1):11-22 (1991).

Nakashita, et al., "Introduction of bacterial metabolism into higher plants by polycistronic transgene expression", *Biosci Biotechnol Biochem.* 65(7):1688-91 (2001).

Nawrath, et al., "Targeting of the polyhydroxybutyrate biosynthetic pathway to the plastids of *Arabidopsis thaliana* results in high levels of polymer accumulation", *Proc. Natl. Acad. Sci. U. S. A.*, 91(26):12760-4 (1994).

Odell, et al., "Identification of DNA sequences required for activity of the cauliflower mosaic virus 35S promoter", *Nature*, 313(6005):810-812 (1985).

Parrish, et al., "The biology and agronomy of switchgrass for biofuels", *Crit. Rev. Plant Sci.*, 24:423-459 (2005).

Peoples, et al., "Poly-3-hydroxybutyrate biosynthesis in *Alcaligenes eutrophus* H16. Characterization of the genes encoding ketothiolase and acetoacetyl-CoA reductase", *J. Biol. Chem.*, 264:15293-15297 (1989).

Perlak, et al., (U.S. Department of Energy and U.S. Department of Agriculture) http://feedstockreview.ornl.gov/pdf/billion_ton_vision.pdf (Accessed online on Jun. 29, 2009).

Perlak, et al., "Modification of the coding sequence enhances plant expression of insect control protein genes", *Proc. Natl. Acad. Sci. USA*, 88(8):3324 (1991).

Petrasovits, et al., "Production of polyhydroxybutyrate in sugarcane", *Plant Biotechnol.*, 5(1):162-172 (2007).

Poirier, et al., "Production of polyhydroxyalkanoates in transgenic plants", *Biopolymers: Polyesters I—Biological Systems and Biotechnological Production*, (Doi and Steinbüchel, eds.), Wiley-VCH: Weinheim, 401-435 (2002).

Purnell, et al., "Spatio-temporal characterization of polyhydroxybutyrate accumulation in sugarcane", *Plant Biotechnol.*, 5(1):173-184 (2007).

Ragauskas, et al., "The path forward for biofuels and biomaterials", *Science*, 311(5760):484-489 (2006).

Richards, et al., "Construction of a GFP-BAR plasmid and its use for switchgrass transformation", *Plant Cell Rep.*, 20(1):48-54 (2001).

Riggs, et al., "Luciferase reporter gene cassettes for plant gene expression studies", *Nucleic Acids Res.*, 15(19):8115 (1987).

Riggs, et al., "Stable transformation of tobacco by electroporation: evidence for plasmid concatenation", *Proc. Natl. Acad. Sci. USA*, 83(15):5602-5606 (1986).

Rinehart, et al., "Tissue-specific and developmental regulation of cotton gene FbL2A. Demonstration of promoter activity in transgenic plants", *Plant Physiol.*, 112(3):1331-1341 (1996).

Sanderson, et al., "Switchgrass as a biofuels feedstock in the USA", *Can. J. Plant Sci.*, 86:1315-1325 (2006).

Saruul, et al., "Production of a biodegradable plastic polymer, β-Hydroxybutyrate, in transgenic Alfalfa", *Crop Sci.*, 42:919-927 (2002).

Schena, et al., "A steroid-inducible gene expression system for plant cells", *Proc. Natl. Acad. Sci. USA*, 88(23):10421-10425 (1991).

Schmer, et al., "Net energy of cellulosic ethanol from switchgrass", *Proc. Natl. Acad Sci USA*, 105(2):464-469 (2008).

Schmidt, et al., "A novel operon organization involving the genes for chorismate synthase (aromatic biosynthesis pathway) and ribosomal GTPase center proteins (L11, L1, L10, L12: rpIKAJL) in cyanobacterium Synechocystis FCC 6803", *J. Biol. Chem.*, 268(36):27447-27457 (1993).

Schnell, et al., "Signal peptide analogs derived from two chloroplast precursors interact with the signal recognition system of the chloroplast envelope", *J. Biol. Chem.*, 266(5):3335-3342 (1991).

Service, R.F., "Cellulosic ethanol. Biofuel researchers prepare to reap a new harvest", *Science*, 315(5818):1488-1491 (2007).

Slater, et al., "Metabolic engineering of *Arabidopsis* and *Brassica* for poly(3-bydroxybutyrate-co-3-hydroxyvalerate) copolymer production", *Nat. Biotechnol.*, 17(10):1011-1016 (1999).

Somleva, "Switchgrass (*Panicum virgatum* L.)", *Agrobacterium Protocols* (Wang, ed.), Humana Press, 2:65-74 (2006).

Somleva, et al., "*Agrobacterium*—Mediated Genetic Transformation of Switchgrass" *Crop Sci.*, 42:2080-2087 (2002).

Staub and Maliga, "Accumulation of D1 polypeptide in tobacco plastids is regulated via the untranslated region of the psbA mRNA", *EMBO J.*, 12(2):601-606 (1993).

Staub and Maliga, "Long regions of homologous DNA are incorporated into the tobacco plastid genome by transformation", *Plant Cell*, 4:39-45 (1992).

Suriyamongkol, et al., "Biotechnological approaches for the production of polyhydroxyalkanoates in microorganisms and plants—a review", *Biotechnol. Adv.*, 25(2):148-175 (2007).

Svab and Maliga, "High-frequency plastid transformation in tobacco by selection for a chimeric aadA gene", *Proc. Natl. Acad Sci. USA*, 90(3):913-917 (1993).

Svab, et al., "Stable transformation of plastids in higher plants", *Proc. Natl. Acad. Sci. USA*, 87(21):8526-8530 (1990).

Valentin, et al., "PHA production, from bacteria to plants", *Int. J. Biol. Macromol.*, 25(1-3):303-306 (1999).

Van Camp, et al., "Tissue-specific activity of two manganese superoxide dismutase promoters in transgenic tobacco", *Plant Physiol.*, 112(2):525-535 (1996).

White, et al., "A cassette containing the bar gene of *Streptomyces hygroscopicus*: a selectable marker for plant transformation", *Nucl. Acids Res.*, 18(4):1062 (1990).

Williams & Peoples, "Biodegradable plastics from plants," *CHEMTECH* 26: 38-44 (1996).

Wrobel, et al., "Polyhydroxybutyrate synthesis in transgenic flax", *J. Biotechnol.*, 107(1):41-54 (2004).

Wrobel-Kwiatkowska, et al., "Engineering of PHB synthesis causes improved elastic properties of flax fibers", *Biotechnol. Prog.*, 23(1):269-277 (2007).

Yamamoto, et al., "Light-responsive elements of the tobacco PSI-D gene are located both upstream and within the transcribed region", *Plant J.*, 12(2):255-265 (1997).

Zhao, et al., "Immunological characterization and chloroplast localization of the tryptophan biosynthetic enzymes of the flowering plant *Arabidopsis thaliana*", *J. Biol. Chem.*, 270(11):6081-6087 (1995).

\* cited by examiner

US 8,487,159 B2

SEQUENCE LISTING

<160> NUMBER OF SEQ ID NOS: 16

<210> SEQ ID NO 1
<211> LENGTH: 26
<212> TYPE: DNA
<213> ORGANISM: Artificial Sequence
<220> FEATURE:
<223> OTHER INFORMATION: Synthetic Primer

<400> SEQUENCE: 1
agatctaccg tcttcggtac gcgctc                                          26

<210> SEQ ID NO 2
<211> LENGTH: 26
<212> TYPE: DNA
<213> ORGANISM: Artificial Sequence
<220> FEATURE:
<223> OTHER INFORMATION: Synthetic Primer

<400> SEQUENCE: 2
ccatggccgc ttggtatctg cattac                                          26

<210> SEQ ID NO 3
<211> LENGTH: 21
<212> TYPE: DNA
<213> ORGANISM: Artificial Sequence
<220> FEATURE:
<223> OTHER INFORMATION: Synthetic Primer

<400> SEQUENCE: 3
gaattcacgg aagatccagg t                                               21

<210> SEQ ID NO 4
<211> LENGTH: 27
<212> TYPE: DNA
<213> ORGANISM: Artificial Sequence
<220> FEATURE:
<223> OTHER INFORMATION: Synthetic Primer

<400> SEQUENCE: 4
agatcttgct gaagctgagc gtgaaag                                         27

<210> SEQ ID NO 5
<211> LENGTH: 24
<212> TYPE: DNA
<213> ORGANISM: Artificial Sequence
<220> FEATURE:
<223> OTHER INFORMATION: Synthetic Primer

<400> SEQUENCE: 5
gcaccatcgt caaccactac atcg                24

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

<400> SEQUENCE: 6
tcatgccagt tcccgtgctt g                   21

<210> SEQ ID NO 7
<211> LENGTH: 22
<212> TYPE: DNA
<213> ORGANISM: Artificial Sequence
<220> FEATURE:
<223> OTHER INFORMATION: Synthetic Primer

<400> SEQUENCE: 7
atcatcgcaa gaccggcaac ag                  22

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
tacaagagct atgccaacgc                     20

<210> SEQ ID NO 9
<211> LENGTH: 22
<212> TYPE: DNA
<213> ORGANISM: Artificial Sequence
<220> FEATURE:
<223> OTHER INFORMATION: Synthetic Primer

<400> SEQUENCE: 9
gcaagaccgg caacaggatt ca                  22

<210> SEQ ID NO 10
<211> LENGTH: 22
<212> TYPE: DNA
<213> ORGANISM: Artificial Sequence
<220> FEATURE:
<223> OTHER INFORMATION: Synthetic Primer

<400> SEQUENCE: 10
tcggcgaggt tgatgtgctg at                  22

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
gtaacataga tgacaccgcg                     20

<210> SEQ ID NO 12
<211> LENGTH: 19
<212> TYPE: DNA
<213> ORGANISM: Artificial Sequence

```
-continued

<220> FEATURE:
<223> OTHER INFORMATION: Synthetic Primer

<400> SEQUENCE: 12
gaaacagcct gaaagtgcc                                                    19

<210> SEQ ID NO 13
<211> LENGTH: 18
<212> TYPE: DNA
<213> ORGANISM: Artificial Sequence
<220> FEATURE:
<223> OTHER INFORMATION: Synthetic Primer

<400> SEQUENCE: 13
gctgggcgat atcaacaa                                                     18

<210> SEQ ID NO 14
<211> LENGTH: 22
<212> TYPE: DNA
<213> ORGANISM: Artificial Sequence
<220> FEATURE:
<223> OTHER INFORMATION: Synthetic Primer

<400> SEQUENCE: 14
gcacatagtt ccataccagg tc                                                22

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
cactggaatg gtcaaggatg                                                   20

<210> SEQ ID NO 16
<211> LENGTH: 19
<212> TYPE: DNA
<213> ORGANISM: Artificial Sequence
<220> FEATURE:
<223> OTHER INFORMATION: Synthetic Primer

<400> SEQUENCE: 16
ctccatgtca tcccagttg                                                    19
```

PRODUCTION OF POLYHYDROXYBUTYRATE IN SWITCHGRASS

CROSS-REFERENCE TO RELATED APPLICATION

This application claims benefit of and priority to U.S. Provisional Patent Application No. 61/048,436 filed on Apr. 28, 2008, and which is incorporated by reference herein in its entirety.

STATEMENT REGARDING FEDERALLY SPONSORED RESEARCH OR DEVELOPMENT

This invention was made with Government Support under Energy Industry of the Future Award No. DE-FC07-11D14214 and Grant No. USDA-68-3A75-3-142 awarded by the United States Department of Agriculture. The Government has certain rights in the invention.

FIELD OF THE INVENTION

The invention is generally related to agricultural biotechnology, in particular to transgenic plants that produce polyhydroxyalkanoates.

BACKGROUND OF THE INVENTION

Fuels, plastics, and chemicals derived from agricultural feedstocks are receiving considerable attention as the world looks for solutions to dwindling non-renewable petroleum resources (Herrera, (2006), *Nature Biotechnol.* 24:755-760; Kanun et al., (2007), *Adv. Biochem. Eng. Biotechnol.* 105:175-204; Ragauskas et al., (2006), *Science* 311:484-489). In the United States, efforts have primarily focused on biofuels such as ethanol produced from the starch in maize kernels. This feedstock will likely be replaced by lignocellulosic biomass since U.S. maize production capacity can only supply a portion of the feedstock required for the widespread production of ethanol (DOE (2006), DOE/SC-0095, U.S. Department of Energy Office of Science and Office of Energy Efficiency and Renewable Energy www.doegenomestolife.org/biofuels/); Service, R. F. (2007) *Science* 315:1488-1491). Current technologies for conversion of lignocellulosic biomass to biofuels are hindered by high costs and a significant amount of research effort is underway to create more efficient, less expensive processes (Service, R. F. (2007) *Science* 315:1488-1491). Engineering bioenergy crops to synthesize industrial materials would provide better economics for both the fuel and co-product components.

Polyhydroxyalkanoates (PHAs), a family of naturally renewable and biodegradable plastics, fit nicely into a biorefinery concept (Kamm et al., (2007), *Adv. Biochem. Eng. Biotechnol.* 105:175-204; Ragauskas et al., (2006), *Science* 311:484-489) as a value added co-product to lignocellulosic derived biofuels. These polymers occur in nature as a storage reserve in some microbes faced with nutrient limitation (Madison et al., (1999) *Microbiol. Mol. Biol. Rev.* 63:21-53) and possess properties enabling their use in a variety of applications currently served by petroleum-based plastics. PHA biobased plastics can be produced via commercial large scale fermentations of microbial strains and the marketing of these plastics in a variety of applications is well under way (Bieles, (2006), *Plastics and Rubber Weekly*, Feb. 17:1; Deligio, (2007), *Modern Plastics*). Since they are inherently biodegradable in soil, compost, and marine environments, they can decrease plastic waste disposal issues. Pathways for production of PHAs have been introduced into a number of crops (for review, see Suriyamongkol et al., (2007), *Biotechnol. Adv.* 25:148-175 and references therein) including maize (Poirier et al., (2002), *Biopolymers: Polyesters I—Biological Systems and Biotechnological Production* (Doi Y and Steinbüchel A eds), pp. 401-435, Weinheim, Wiley-VCH), sugarcane (Petrasovits et al., (2007), *Plant Biotechnol.* 5:162-172; Purnell et al., (2007), *Plant Biotechnol.* 5:173'-184), flax (Wrobel-Kwiatkowska et al., (2007), *Biotechnol. Prog.* 23:269-277; Wrobel et al., (2004), *J. Biotechnol.* 107:41-54), cotton (John et al., (1996), *Proc. Natl. Acad Sci. USA* 93:12768-12773), alfalfa (Saruul et al., (2002), *Crop Sci.* 42:919-927), tobacco (Arai et al., (2001), *Plant Biotechnol.* 18:289-293; Bohmert et al., (2002), *Plant Physiol.* 128:1282-1290; Lössl et al., (2005), *Plant Cell Physiol.* 46:1462-1471; Lössl et al., (2003), *Plant Cell Rep.* 21:891-899), potato (Bohmert et al., (2002), *Plant Physiol.* 128:1282-1290), and oilseed rape (Houmiel et al., (1999), *Planta* 209:547-550; Slater et al., (1999), *Nat. Biotechnol.* 17:1011-1016; Valentin et al., (1999), *Int. J. Biol. Macromol.* 25:303-306) resulting in the production of a range of polymer levels depending on the crop and mode of transformation. See also U.S. Pat. No. 5,663,063 to Peoples et al., and U.S. Pat. No. 5,534,432 to Peoples et al. To date, significant PHA production has only been demonstrated in plants with a C3 photosynthetic pathway (i.e., *Arabidopsis*, *Brassica*) or a C4 NADP-malic enzyme photosynthetic pathway (corn, sugarcane) that produce storage products such as oils or carbohydrates. Production of polymer in plants with a C4 NAD-malic enzyme photosynthetic pathway such as switchgrass has not been demonstrated. Moreover, PHB production greater than 0.3% dwt (dry weight) has only been reported in plants that produce storage materials such as oils or carbohydrates. It is unknown whether plants that do not produce storage products can be engineered to produce PHAs in commercially useful amounts.

Switchgrass is one of the bioenergy crops targeted by the United States Department of Energy (DOE (2006), U.S. Department of Energy Office of Science and Office of Energy Efficiency and Renewable Energy (www.doegenomestolife.org/biofuels/); Sanderson et al., (2006), *Can. J. Plant Sci.* 86:1315-1325). Recent studies suggest that production of cellulosic ethanol from this crop nets 540% more renewable energy than the required nonrenewable energy inputs (Schmer, et al., (2008), *Proc. Natl. Acad Sci USA* 105:464-469). Despite the considerable interest in application of genomics and transgenic approaches for improvement of switchgrass for biofuel production (Bouton, (2007), *Current Opinion in Genetics & Development* 17:553-558), only the expression of reporter and selectable marker genes has been described (Richards et al., (2001), *Plant Cell Rep.* 20:48-54; Somleva et al., (2002), *Crop Sci.* 42:2080-2087). Additionally, switchgrass does not produce storage products such as oils or carbohydrates, and thus would not be expected to accumulate PHA.

SUMMARY OF THE INVENTION

Transgenic plants, plant material, and plant cells for synthesis of polyhydroxyalkanoates, preferably poly(3-hydroxybutyrate) (also referred to as P3HB or PHB), have been developed. Preferred plants that can be genetically engineered to produce PHB include plants that do not produce storage products such as oils and carbohydrates and plants that have a $C_4$ NAD-malic enzyme photosynthetic pathway. Such plants also advantageously produce lignocellulosic biomass that can be converted into biofuels. An exemplary plant that can be genetically engineered to produce PHB and produces lignocellulosic biomass is switchgrass, *Panicum virgatum* L. A preferred cultivar of switchgrass is Alamo. Other suitable cultivars of switchgrass include Blackwell, Kanlow, Nebraska 28, Pathfinder, Cave-in-Rock, Shelter and Trailblazer.

In one embodiment, the invention provides transgenic plants for the production of polyhydroxyalkanoates.

In another embodiment, the invention provides transgenic plants for the production of polyhydroxyalkanoates wherein the plants have a $C_4$ NAD-malic enzyme photosynthetic pathway.

The invention also provides transgenic plants for the production of polyhydroxyalkanoates wherein the plants do not produce storage products such as oils and carbohydrates.

Another embodiment provides methods, constructs and genetically engineered plants for producing polyhydroxyalkanoates using transgenic plants.

In one embodiment, a plant, plant tissue, or plant material capable of producing lignocellulosic biomass is engineered to express genes encoding enzymes in the PHA biosynthetic pathway. The preferred PHA is P3HB. Genes useful for production of P3HB include phaA, phaB, and phaC, all of which are known in the art. The genes can be introduced in the plant, plant tissue, or plant cells using conventional plant molecular biology techniques.

Another embodiment provides a transgenic plant genetically engineered to produce at least about 1% dry weight (dwt) polyhydroxyalkanoate, wherein the corresponding non-transgenic plant does not produce storage material. Preferably the transgenic plant is a $C_4$ plant with the $C_4$ NAD-malic enzyme photosynthetic pathway. A preferred transgenic plant is switchgrass engineered with heterologous genes encoding a thiolase, a reductase, and a PHA synthase for the production of poly(3-hydroxybutyrate).

Another embodiment provides seeds of the disclosed transgenic plants.

Still another embodiment provides feedstock from the disclosed transgenic plants. The feedstock typically contains at least about 1 to about 4% PUB and lignocellulosic biomass from plants that do not produce storage materials.

Yet another embodiment provides a method for increasing the transformation efficiency by inducing mature caryopses to dedifferentiate into embryogenic callus cultures, identifying the embryogenic callus cultures capable of producing about 300 or more plantlets per gram of callus, and transforming the embryogenic callus. Typically, the plant or plant tissue is transformed to produce PHB.

BRIEF DESCRIPTION OF THE DRAWINGS

FIG. 1b shows detection of inserted T-DNA and flanking regions in genomic DNA of selected switchgrass lines by Southern blot hybridization. Abbreviations are as follows: LB, left T-DNA border sequence; RB, right T-DNA border sequence; cab5/hsp70, cab-m5 promoter fused to the hsp70 intron; TS, plastid targeting sequence consisting of the signal peptide of the small subunit of rubisco from pea and the first 24 amino acids of the mature protein (Cashmore, (1983), *Genetic Engineering of Plants* (Kosuge T, Meredith C P and Hollaender A eds), pp. 29-38, New York, Plenum; Kourtz et al., (2005), *Plant Biotechnol.* 3:435-447); phaC, gene encoding PHA synthase; nos, 3' terminator of the nopaline synthase gene (Bevan et al., (1983), Nucleic Acids Res. 11:369-385); phaA, gene encoding thiolase; phaB, gene encoding reductase; e35S/hsp70, double enhanced version of the 35S promoter from cauliflower mosaic virus fused to the hsp70 intron; bar, gene encoding phosphinotricin acetyltransferase imparting resistance to bialaphos. The location of Sac I sites used in Southern blot hybridization experiments are indicated in FIG. 1. Regions amplified by PCR for identification of primary transformants are indicated by a line below the gene. The digoxigenin-labeled PCR products for the phaB and bar genes were used as probes for DNA hybridizations. For plasmid pMBXS159, the cab5 promoter/hsp70 fragment is replaced by a rubi2 promoter fragment.

DETAILED DESCRIPTION OF THE INVENTION

I. Definitions

Figure 1:
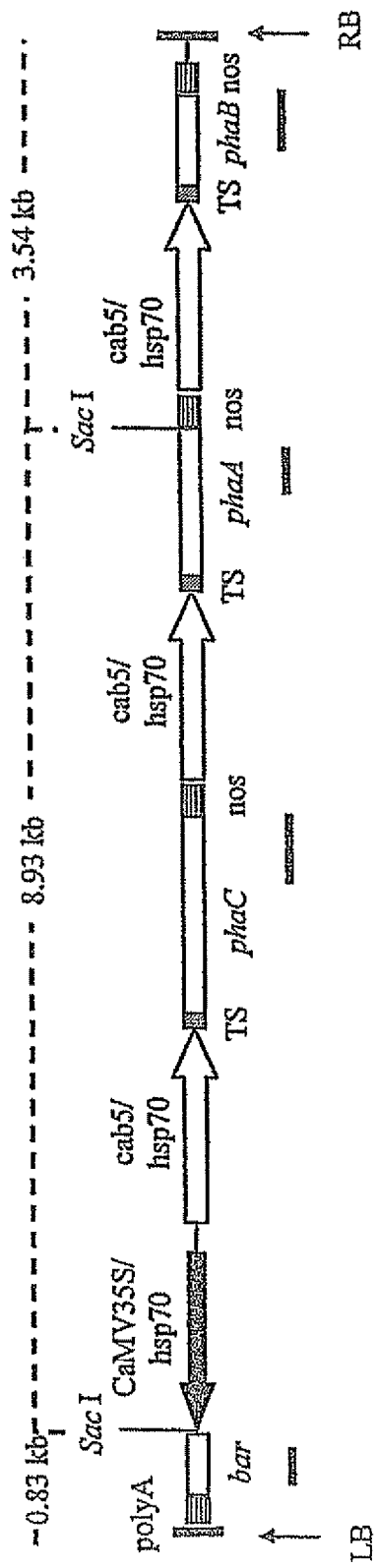
FIG. 1 is a schematic diagram of expression cassettes within the T-DNA border sequences of the 19.55-kb transformation construct pMBXS155.

A number of terms used herein are defined and clarified in the following section.

The term "PHA copolymer" refers to a polymer composed of at least two different hydroxyalkanoic acid monomers.

The term "PHA homopolymer" refers to a polymer that is composed of a single hydroxyalkanoic acid monomer.

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences.

As used herein, an "expression control sequence" is a DNA sequence that controls and regulates the transcription and/or translation of another DNA sequence.

As used herein, "operably linked" means incorporated into a genetic construct so that expression control sequences effectively control expression of a coding sequence of interest.

As used herein, "transformed" and "transfected" encompass the introduction of a nucleic acid (e.g., a vector) into a cell by a number of techniques known in the art.

"Plasmids" are designated by a lower case "p" preceded and/or followed by capital letters and/or numbers.

As used herein the term "heterologous" means from another host. The other host can be the same or different species.

The term "plant" is used in it broadest sense. It includes, but is not limited to, any species of woody, ornamental or decorative, crop or cereal, fruit or vegetable plant, and photosynthetic green algae (e.g., *Chlamydomonas reinhardtii*). It also refers to a plurality of plant cells that is largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture. The term "plant part" as used herein refers to a plant structure, a plant organ, or a plant tissue.

A "non-naturally occurring plant" refers to a plant that does not occur in nature without human intervention. Non-naturally occurring plants include transgenic plants and plants produced by non-transgenic means such as plant breeding.

The term "plant cell" refers to a structural and physiological unit of a plant, comprising a protoplast and a cell wall. The plant cell may be in the form of an isolated single cell or a cultured cell, or as a part of a higher organized unit such as, for example, a plant tissue, a plant organ, or a whole plant.

The term "plant cell culture" refers to cultures of plant units such as, for example, protoplasts, cell culture cells, cells in plant tissues, pollen, pollen tubes, anthers, ovules, embryo sacs, zygotes and embryos at various stages of development.

The term "plant material" refers to leaves, stems, roots, flowers or flower parts, fruits, pollen, anthers, egg cells, zygotes, seeds, cuttings, cell or tissue cultures, or any other part or product of a plant.

A "plant organ" refers to a distinct and visibly structured and differentiated part of a plant such as a root, stem, leaf, flower bud, inflorescence, seed or embryo.

"Storage material" with regard to plants refers to the storage of oils and carbohydrates.

Plants that "do not produce storage materials" refers to plants that do not have specialized tissues or organs for storing oil and/or carbohydrate in excess of that needed for general day-to-day metabolism of the plant.

The term "non-transgenic plant" refers to a plant that has not been genetically engineered to produce polyhydroxyalkanoates. A "corresponding non-transgenic plant" refers to the plant prior to the introduction of heterologous nucleic acids that encode enzymes for producing polyhydroxyalkanoates.

II. Transgenic Plants for Producing PHAs

A. Representative Plants for Genetic Engineering

It has been discovered that plants that do not produce storage materials such as oils and carbohydrates can be genetically engineered to produce and accumulate polyhydroxyalkanoates in significant amounts. A preferred plant is switchgrass *Panicum virgatum* L. "Significant amounts" refers to amounts of PHA or PHB of more than about 1%, 2%, or 3% dry weight (dwt) of plants, for example plants grown in soil rather than plant material from cell culture. In certain embodiments the disclosed transgenic plants produce and accumulate at least about 4% dwt PHA. A preferred PHA is poly(3-hydroxybutyrate).

The accumulation of PHA in amounts from 1% to 4% dwt or more in transgenic plants has previously only been achieved in plants that produce storage materials such as oils and carbohydrates. It was unexpectedly discovered that plants that do not produce storage materials such as oils and carbohydrates can be engineered to produce and accumulate PHA in amounts comparable to or even greater than plants that produce storage materials.

Thus, one embodiment provides a transgenic plant that does not produce storage products and accumulates at least about 3.7% dwt PHA, preferably in primary transformants. Another embodiment provides a transgenic plant that does not produce storage products and produces at least about 4% dwt PHA, preferably in plants obtained from controlled crosses of transgenic PHA producers. Still another embodiment provides a transgenic plant that does not produce storage products and accumulates from about 1% to about 4% dwt PHA. The percentage of PHA can be at least about 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0% dwt or more. In other embodiments, the percent of PHA can be at least about 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, or 7.0% dwt or more.

Still another embodiment provides transgenic switchgrass genetically engineered to produce and accumulate at least about 1% to at least about 4% dwt PHA, preferably PHB. Switchgrass contains the $C_4$ NAD-malic enzyme photosynthetic pathway ("$C_4$ plants") which provides additional advantages.

$C_4$ Plants $C_4$ plants have a competitive advantage over plants possessing the more common $C_3$ carbon fixation pathway under conditions of drought, high temperatures and nitrogen limitation. $C_4$ carbon fixation has evolved on up to 40 independent occasions in different groups of plants, making it an example of convergent evolution. Plants with $C_4$ metabolism include sugarcane, maize, Sorghum, finger millet, switchgrass, *Miscanthus*, and amaranth. $C_4$ plants represent about 5% of Earth's plant biomass and 1% of its known plant species. However, they account for around 30% of terrestrial carbon fixation. These species are concentrated in the tropics (below latitudes of 45°) where the high air temperature contributes to higher possible levels of oxygenase activity by Rubisco, which increases rates of photorespiration in $C_3$ plants. Suitable $C_4$ plants include those that do not produce storage materials such as oils and carbohydrates. Representative $C_4$ plants that do not produce storage materials and that can be genetically engineered to produce PHA at significant levels include, but are not limited to switchgrass.

Additionally, $C_4$ plants produce lignocellulosic biomass. Lignocellulosic biomass has received considerable attention as an abundant feedstock for biofuels despite the high costs associated with conversion processes. The United States has the agricultural capability to grow vast quantities of this biomass, with recent estimates exceeding one billion tons without affecting food or feed (Perlack et al., (U.S. Department of Energy and U.S. Department of Agriculture) http://feedstockreview.ornl.gov/pdf/billion_ton_vision.pdf). These estimates include 377 million dry tons of biomass from perennial herbaceous crops that could be dedicated for conversion to biofuels.

A preferred plant to produce PHA is switchgrass, *Panicum virgatum* L. Switchgrass is a $C_4$ perennial grass with high biomass yields. It is a warm season perennial grass, has great potential as an industrial crop in that it requires minimal inputs for growth in many agricultural regions of the United States and Europe (Lewandowski et al., (2003), *Biomass Bioenerg.* 25:335-361) and has the ability to sequester large amounts of carbon in the soil with its extensive root system (Parrish et al., (2005), *Crit. Rev. Plant Sci.* 24:423-459). Direct production of biobased polymers in switchgrass would yield an industrial plant feedstock that could be converted into plastics and fuels, providing better economics for both co-products.

Both upland and lowland switchgrass cultivars can be used, including but not limited to Alamo, Blackwell, Kanlow, Nebraska 28, Pathfinder, Cave-in-Rock, Shelter and Trailblazer.

B. Genes for Producing PHB

Genes encoding the enzymes necessary for producing PHA including PHB are known in the art (Madison and Huisman, (1999), *Microbiol. Mol. Biol. Rev.,* 63(1):21-53). The PHB biosynthetic pathway requires three enzymatic reactions catalyzed by the following three genes: phaA, phaB, and phaC. The first reaction is the condensation of two acetyl coenzyme A (acetyl-CoA) molecules into acetoacetyl-CoA by β-ketoacyl-CoA thiolase (EC 2.3.1.9) encoded by phaA. The second reaction is the reduction of acetoacetyl-CoA to (R)-3-hydroxybutyryl-CoA by an NADPH-dependent acetoacetyl-CoA reductase (EC 1.1.1.36) encoded by phaB. The (R)-3-hydroxybutyryl-CoA monomers are polymerized into poly(3-hydroxybutyrate) by a PHB synthase encoded by phaC. Sources of these enzymes include, but are not limited to, *Zoogloea ramigera, Ralstonia eutropha, Acinetobacter* spp., *Alcaligenes latus, Pseudomonas acidophila, Paracoccus denitrificans, Rhizobium meliloti, Chromatium vinosum, Thiocystis violacea*, and *Synechocytis*.

In one embodiment, the PHB genes chosen for this construct include a hybrid *Pseudomonas oleovorans/Zoogloea ramigera* PHA synthase (U.S. Pat. No. 6,316,262 to Huisman et al.) and the thiolase and reductase from *Ralstonia eutropha* (Peoples et al., (1989), *J. Biol. Chem.* 264:15293-15297).

III. Plant Transformation Technology

A. Transformation of Plants with PHA Genes.

Transgenic plants for producing PHA, in particular PHB, can be produced using conventional techniques to express phaA, phaB, and phbC in plants or plant cells (*Methods in Molecular Biology*, vol. 286, Transgenic Plants: Methods and Protocols Edited by L. Pena, Humana Press, Inc. Totowa, N.J. (2005)). Typically, gene transfer, or transformation, is carried out using explants capable of regeneration to produce complete, fertile plants. Generally, a DNA or an RNA molecule to be introduced into the organism is part of a transformation vector. A large number of such vector systems known in the art may be used, such as plasmids. The components of the expression system can be modified, e.g., to increase expression of the introduced nucleic acids. For example, truncated sequences, nucleotide substitutions or other modifications may be employed. Expression systems known in the art may be used to transform virtually any plant cell under suitable conditions. A transgene comprising a DNA molecule encoding the genes for PHA production is preferably stably transformed and integrated into the genome of the host cells. Transformed cells are preferably regenerated into whole plants. Detailed description of transformation techniques are within the knowledge of those skilled in the art.

B. Reporter Genes and Selectable Marker Genes

Reporter genes or selectable marker genes may be included in the expression cassette. Examples of suitable reporter genes known in the art can be found in, for example, Jefferson et al. (1991) in *Plant Molecular Biology Manual*, ed. Gelvin et al. (Kluwer Academic Publishers), pp. 1-33; DeWet et al., (1987), *Mol Cell. Biol.* 7:725-737; Goff et al., (1990), *EMBO J.* 9:2517-2522; Kain et al., (1995), *Bio Techniques* 19:650-655; and Chiu et al., (1996), *Current Biology* 6:325-330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al., (1983), *EMBO J.* 2:987-992; methotrexate (Herrera Estrella et al., (1983), *Nature* 303:209-213; Meijer et al., (1991), *Plant Mol Biol.* 16:807-820); hygromycin (Waldron et al., (1985), *Plant Mol. Biol.* 5:103-108; Zhijian et al., (1995), *Plant Science* 108:219-227); streptomycin (Jones et al., (1987), *Mol. Gen. Genet.* 210:86-91); spectinomycin (Bretagne-Sagnard et al., *Transgenic Res.* 5:131-137 (1996)); bleomycin (Hille et al., (1990), *Plant Mol. Biol,* 7:171-176); sulfonamide (Guerineau et al., (1990), *Plant Mol. Biol.* 15:127-136); bromoxynil (Stalker et al., (1988), *Science* 242:41 9423); glyphosate (Shaw et al., (1986), *Science* 233:478-481); phosphinothricin (DeBlock et al., (1987), *EMBO J.* 6:2513-2518).

Other genes that could be useful in the recovery of transgenic events but might not be required in the final product include, but are not limited to, GUS (b-glucoronidase (Jefferson, (1987), *Plant Mol. Biol. Rep.* 5:387), GFP (green fluorescent protein) (Chalfie et al., (1994), *Science* 263:802), luciferase (Riggs et al., (1987), *Nucleic Acids Res.* 15(19): 8115; Luehrsen et al., (1992), *Methods Enzymol.* 216:397-414) and the maize genes encoding for anthocyanin production (Ludwig et al., (1990), *Science* 247:449).

The expression cassette including a promoter sequence operably linked to a heterologous nucleotide sequence of interest, for example encoding a PHA synthase, a thiolase, and/or a reductase can be used to transform any plant.

C. Transformation Protocols

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al., (1986), *Biotechniques* 4:320-334), electroporation (Riggs et al., (1986), *Proc. Natl. Acad. Sci. USA* 83:5602-5606), *Agrobacterium*-mediated transformation (U.S. Pat. No. 5,563,055 to Townsend, et al.; WO US98/01268 to Zhao et al.) and direct gene transfer (Paszkowski et al., (1984), *EMBO J.* 3:2717-2722) by microprojectile bombardment (see, for example, U.S. Pat. No. 4,945,050 to Sanford et al.; Tomes et al. (1995), *Plant Cell, Tissue, and Organ Culture: Fundamental Methods*, ed. Gamborg and Phillips (Springer-Verlag, Berlin); and McCabe et al., (1988), *Biotechnology* 6:923-926). Also see Weissinger et al. (1988), *Ann. Rev. Genet.* 22:421-477; Sanford et al., (1987), *Particulate Science and Technology* 5:27-37 (onion); Christou et al., (1988), *Plant Physiol.* 87:671-674 (soybean); McCabe et al., (1988), *BioTechnology* 6:923-926 (soybean); Finer and McMullen, (1991), *In Vitro Cell Dev. Biol.* 27P:175-182 (soybean); Singh et al., (1998), *Theor. Appl. Genet.* 96:319-324 (soybean); Dafta et al. (1990) *Biotechnology* 8:736-740 (rice); Klein et al. (1988), *Proc. Natl.*

Acad. Sci. USA 85:4305-4309 (maize); Klein et al., (1988), Biotechnology 6:559-563 (maize); U.S. Pat. No. 5,240,855 to Tomes; U.S. Pat. Nos. 5,322,783 and 5,324,646 to Buising et al.; Tomes et al. (1995) in *Plant Cell, Tissue, and Organ Culture: Fundamental Methods*, ed. Gamborg (Springer-Verlag, Berlin) (maize); Klein et al., (1988), *Plant Physiol.* 91:440-444 (maize); Fromm et al., (1990), *Biotechnology* 8:833-839 (maize); Hooykaas-Van Slogteren et al., (1984), *Nature* 311:763-764; Bowen et al., U.S. Pat. No. 5,736,369 (cereals); Bytebier et al., (1987), *Proc. Natl. Acad. Sci. USA* 84:5345-5349 (Liliaceae); De Wet et al., (1985), in *The Experimental Manipulation of Ovule Tissues*, ed. Chapman et al. (Longman, N.Y.), pp. 197-209 (pollen); Kaeppler et al., (1990), *Plant Cell Reports* 9:415-418 and Kaeppler et al., (1992), *Theor. Appl. Genet.* 84:560-566 (whisker-mediated transformation); D'Halluin et al., (1992), *Plant Cell* 4:1495-1505 (electroporation); Li et al., (1993), *Plant Cell Reports* 12:250-255 and Christou and Ford, (1995), *Annals of Botany* 75:407-413 (rice); Osjoda et al., (1996), *Nature Biotechnology* 14:745-750 (maize via *Agrobacterium tumefaciens*).

The transformed cells are grown into plants in accordance with conventional techniques. See, for example, McCormick et al., (1986), *Plant Cell Reports* 5:81-84. These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

D. Modulating Expression of Genes in Plants

1. Inducible Promoters

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize 1n2-2 promoter, which is activated by benzenesulfonamide herbicide safeners, the maize GST promoter, which is activated by hydrophobic electrophilic compounds that are used as pre-emergent herbicides, and the tobacco PR-1 promoter, which is activated by salicylic acid. Other chemical-regulated promoters include steroid-responsive promoters (see, for example, the glucocorticoid-inducible promoter in Schena et al., (1991), *Proc. Natl. Acad. Sci. USA* 88:10421-10425 and McNellis et al., (1998), *Plant J.* 14(2): 247-257) and tetracycline-inducible and tetracycline-repressible promoters (see, for example, Gatz et al., (1991), *Mol. Gen. Genet.* 227:229-237, and U.S. Pat. Nos. 5,814,618 and 5,789,156), herein incorporated by reference in their entirety.

In one embodiment, coordinated expression of the three transgenes, phaA, phaB, and phaC, necessary for conversion of acetyl-CoA to PHB, is controlled by the maize light inducible cab-m5 promoter in multi-gene expression constructs (Sullivan et al., (1989); *Mol. Gen. Genet.*, 215:431-440; Becker et al., (1992), *Plant Mol. Biol.*, 20:49-60). The promoter can be fused to the hsp70 intron (U.S. Pat. No. 5,593,874 to Brown et al.) for enhanced expression in monocots. It has been previously shown that plants transformed with multi-gene constructs produced higher levels of polymer than plants obtained from crossing single transgene lines (Bohmert et al., (2000), *Planta* 211:841-845; Valentin et al., (1999), *Int. J. Biol. Macromol.* 25:303-306).

2. Constitutive Promoters

Constitutive promoters include, for example, the core promoter of the Rsyn7 promoter and other constitutive promoters disclosed in WO 99/43838 and U.S. Pat. No. 6,072,050; the core CAMV 35S promoter (Odell et al., (1985), *Nature* 313: 810-812); rice actin (McElroy et al., (1990), *Plant Cell* 2:163-171); ubiquitin (Christensen et al., (1989), *Plant Mol. Biol.* 12:619-632 and Christensen et al., (1992), *Plant Mol. Biol.* 18:675-689); pEMU (Last et al., (1991), *Theor. Appl. Genet.* 81:581-588); MAS (Velten et al., (1984), *EMBO J.* 3:2723-2730); ALS promoter (U.S. Pat. No. 5,659,026). Other constitutive promoters are described in U.S. Pat. Nos. 5,608,149; 5,608,144; 5,604,121; 5,569,597; 5,466,785; 5,399,680; 5,268,463; and 5,608,142.

In one embodiment, coordinated expression of the three transgenes, phaA, phaB, and phaC, necessary for conversion of acetyl-CoA to PHB is controlled by the constitutive rice ubiquitin 2 promoter in multi-gene expression constructs.

3. Weak Promoters

Where low level expression is desired, weak promoters may be used. Generally, the term "weak promoter" is intended to describe a promoter that drives expression of a coding sequence at a low level. "Low level" refers to levels of about $1/1000$ transcripts to about $1/100,000$ transcripts to about $1/500,000$ transcripts. Alternatively, it is recognized that weak promoters also encompass promoters that are expressed in only a few cells and not in others to give a total low level of expression. Where a promoter is expressed at unacceptably high levels, portions of the promoter sequence can be deleted or modified to decrease expression levels.

Such weak constitutive promoters include, for example, the core promoter of the Rsyn7 promoter (WO 99/43838 and U.S. Pat. No. 6,072,050).

Preferred promoters include, but are not limited to, constitutive rice ubiquitin 2 or the maize light inducible cab-m5 promoter.

4. Tissue Specific Promoters

"Tissue-preferred" promoters can be used to target gene expression within a particular tissue. Tissue-preferred promoters include those described by Yamamoto et al., (1997), *Plant J.* 12(2)255-265; Kawamata et al., (1997), *Plant Cell Physiol.* 38(7):792-803; Hansen et al., (1997), *Mol. Gen. Genet.* 254(3):337-343; Russell et al., (1997), *Transgenic Res.* 6(2):157-168; Rinehart et al., (1996), *Plant Physiol.* 112(3):1331-1341; Van Camp et al., (1996), *Plant Physiol.* 112(2):525-535; Canevascini et al., (1996), *Plant Physiol.* 112(2):513-524; Yamamoto et al., (1994), *Plant Cell Physiol.* 35(5):773-778; Lam, (1994), *Results Probl. Cell Differ.* 20:181-196; Orozoo et al., (1993), *Plant Mol. Biol.* 23(6): 1129-1138; Matsuoka et al., (1993), *Proc. Natl. Acad. Sci. USA* 90(20):9586-9590; and Guevara-Garcia et al. (1993), *Plant J.* 4(3):495-505. Such promoters can be modified, if necessary, for weak expression.

i. Seed Specific Promoters

"Seed-preferred" promoters include both "seed-specific" promoters (those promoters active during seed development such as promoters of seed storage proteins) as well as "seed-germinating" promoters (those promoters active during seed germination). See Thompson et al., *BioEssays* 10:108 (1989), herein incorporated by reference. Such seed-preferred promoters include, but are not limited to, Cim1 (cytokinin-induced message); cZ19B1 (maize 19 kDa zein); milps (myo-inositol-1-phosphate synthase); and ce1A (cellulose synthase). Gamma-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, and globulin 1.

ii. Leaf Specific Promoters

Leaf-specific promoters are known in the art. See, for example, Yamamoto et al., (1997), *Plant J.* 12(2):255-265; Kwon et al., (1994), *Plant Physiol.* 105:357-67; Yamamoto et al., (1994), *Plant Cell Physiol.* 35(5):773-778; Gotor et al., (1993), *Plant J.* 3:509-18; Orozco et al., (1993), *Plant Mol. Biol.* 23(6):1129-1138; and Matsuoka et al., (1993), *Proc. Natl. Acad. Sci. USA* 90(20):9586-9590.

iii. Root Specific Promoters

Root-preferred promoters are known and may be selected from the many available from the literature or isolated de novo from various compatible species. See, for example, Hire et al. (1992), *Plant Mol. Biol.* 20(2):207-218 (soybean root-specific glutamine synthetase gene); Keller and Baumgartner, (1991), *Plant Cell* 3(10):1051-1061 (root-specific control element in the GRP 1.8 gene of French bean); Sanger et al., (1990), *Plant Mol. Biol.* 14(3):433-443 (root-specific promoter of the mannopine synthase (MAS) gene of *Agrobacterium tumefaciens*); and Miao et al. (1991), *Plant Cell* 3(1):11-22 (full-length cDNA clone encoding cytosolic glutamine synthetase (GS), which is expressed in roots and root nodules of soybean). See also U.S. Pat. Nos. 5,837,876; 5,750,386; 5,633,363; 5,459,252; 5,401,836; 5,110,732; and 5,023,179.

5. Combinations of Promoters

Certain embodiments use transgenic plants or plant cells having multi-gene expression constructs having more than one promoter. The promoters can be the same or different.

D. Chloroplast Targeting Sequences

In one embodiment, the chloroplast was chosen as the site for PHB synthesis in switchgrass since this organelle has an endogenous flux of the polymer precursor acetyl-CoA for fatty acid biosynthesis and has yielded the highest levels of polymer in plants to date (Bohmert et al., (2000) *Molecular Biology and Biotechnology of Plant Organelles* (Daniell H and Chase C D eds), pp. 559-585, Netherlands, Kluwer Academic Publishers; Bohmert et al., (2004), *Molecular Biology and Biotechnology of Plant Organelles* (Daniell H and Chase C D eds), pp. 559-585, Netherlands, Kluwer Academic Publishers).

Chloroplast targeting sequences are known in the art and can be found at the N-terminus of proteins including the small subunit of ribulose-1,5-bisphosphate carboxylase (Rubisco) (de Castro Silva Filho et al., (1996), *Plant Mol. Biol.* 30:769-780; Schnell et al., (1991), *J. Biol. Chem.* 266(5):3335-3342); 5-(enolpyruvyl)shikimate-3-phosphate synthase (EPSPS) (Archer et al., (1990), *J. Bioenerg. Biomemb.* 22(6):789-810); tryptophan synthase (Zhao et al., (1995), *J. Biol. Chem.* 270 (11):6081-6087); plastocyanin (Lawrence et al., (1997), *J. Biol. Chem.* 272(33):20357-20363); chorismate synthase (Schmidt et al., (1993), *J. Biol. Chem.* 268(36):27447-27457); and the light harvesting chlorophyll a/b binding protein (LHBP) (Lamppa et al., (1988), *J. Biol. Chem.* 263:14996-14999). See also Von Heijne et al., (1991), *Plant Mol. Biol. Rep.* 9:104-126; Clark et al., (1989), *J. Biol. Chem.* 264:17544-17550; Della-Cioppa et al., (1987), *Plant Physiol* 84:965-968; Romer et al., (1993), *Biochem. Biophys. Res. Commun.* 196:1414-1421; and Shah et al., (1986), *Science* 233:478-481.

E. Methods for Transforming Chloroplasts

An alternative method for engineering PHB production in plants is direct integration of the genes of interest into the chloroplast genome.

Methods for transformation of chloroplasts are known in the art. See, for example, Svab et al., (1990), *Proc. Natl. Acad. Sci. USA* 87:8526-8530; Svab and Maliga, (1993), *Proc. Natl. Acad. Sci. USA* 90:913-917; Svab and Maliga, (1990), *EMBO J.* 12:601-606. The method relies on particle gun delivery of DNA containing a selectable marker and targeting of the DNA to the plastid genome through homologous recombination. Additionally, plastid transformation may be accomplished by transactivation of a silent plastid-born transgene by tissue-preferred expression of a nuclear-encoded and plastid-directed RNA polymerase. Such a system was reported in McBride et al., (1994), *Proc. Natl. Acad. Sci. USA* 91:7301-7305.

Plastid transformation technology is extensively described in U.S. Pat. Nos. 5,451,513; 5,545,817; and 5,545,818, in WO 95/16783, and in McBride et al., (1994), *Proc. Natl. Acad. Sci. USA* 91:7301-7305. A basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab, Z., Hajdukiewicz, P., and Maliga, P., (1990), *Proc. Natl. Acad, Sci. USA* 87:8526-8530; Staub, J. M., and Maliga, P., (1992), *Plant Cell* 4:39-45). The presence of cloning sites between these markers allows creation of a plastid targeting vector for introduction of foreign DNA molecules (Staub, J. M., and Maliga, P., (1993), *EMBO J.* 12:601-606). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab, Z., and Maliga, P., (1993), *Proc. Natl. Acad. Sci. USA* 90:913-917). This marker has been used successfully for high-frequency transformation of the plastid genome of the green alga *Chlamydomonas reinhardtii* (Goldschmidt-Clermont, M., (1991), *Nucl. Acids Res.* 19:4083-4089). Other selectable markers useful for plastid transformation are known in the art.

The nucleic acids of interest to be targeted to the chloroplast may be optimized for expression in the chloroplast to account for differences in codon usage between the plant nucleus and this organelle. Modification of the gene encoding sequence to contain chloroplast-preferred codons is described in U.S. Pat. No. 5,380,831.

F. Requirements for Construction of Plant Expression Cassettes

Nucleic acid sequences intended for expression in transgenic plants are first assembled in expression cassettes behind a suitable promoter active in plants. The expression cassettes may also include any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be transferred to the plant transformation vectors described infra. The following is a description of various components of typical expression cassettes.

1. Transcriptional Terminators

A variety of transcriptional terminators are available for use in expression cassettes. These are responsible for the termination of transcription beyond the transgene and the correct polyadenylation of the transcripts. Appropriate transcriptional terminators are those that are known to function in plants and include the CaMV 35S terminator, the tm1 terminator, the nopaline synthase terminator and the pea rbcS E9 terminator. These are used in both monocotyledonous and dicotyledonous plants.

2. Sequences for the Enhancement or Regulation of Expression

Numerous sequences have been found to enhance gene expression from within the transcriptional unit and these sequences can be used in conjunction with the genes to increase their expression in transgenic plants. For example, various intron sequences such as introns of the maize Adh1 gene have been shown to enhance expression, particularly in monocotyledonous cells. In addition, a number of non-translated leader sequences derived from viruses are also known to enhance expression, and these are particularly effective in dicotyledonous cells.

G. Coding Sequence Optimization

The coding sequence of the selected gene may be genetically engineered by altering the coding sequence for optimal expression in the crop species of interest. Methods for modifying coding sequences to achieve optimal expression in a particular crop species are well known (see, e.g., Perlak et al., (1991), *Proc. Natl. Acad. Sci. USA* 88:3324; and Koziel et al., (1993), *Biotechnol.* 11:194).

H. Construction of Plant Transformation Vectors

Numerous transformation vectors available for plant transformation are known to those of ordinary skill in the plant transformation arts. The genes pertinent to this disclosure can be used in conjunction with any such vectors. The selection of vector depends upon the selected transformation technique and the target species for transformation. For certain target species, different antibiotic or herbicide selection markers are preferred. Selection markers used routinely in transformation include the npt11 gene, which confers resistance to kanamycin and related antibiotics (Messing & Vierra, (1982), *Gene* 19:259-268, Bevan et al., (1983), *Nature* 304:184-187), the bar gene, which confers resistance to the herbicide phosphinothricin (White et al., (1990), *Nucl. Acids Res.* 18:1062, Spencer et al., (1990), *Theor. Appl. Genet.* 79:625-631), the hph gene, which confers resistance to the antibiotic hygromycin (Blochinger & Diggelmann, (1984), *Mol. Cell. Biol.* 4:2929-2931), the mana gene, which allows for positive selection in the presence of mannose (Miles and Guest, (1984), *Gene* 32:41-48; U.S. Pat. No. 5,767,378), the dhfr gene, which confers resistance to methotrexate (Bourouis et al., (1983), *EMBO J.* 2(7):1099-1104), and the EPSPS gene, which confers resistance to glyphosate (U.S. Pat. Nos. 4,940,935 and 5,188,642).

Many vectors are available for transformation using *Agrobacterium tumefaciens*. These typically carry at least one T-DNA sequence and include vectors such as pBIN19. Typical vectors suitable for *Agrobacterium* transformation include the binary vectors pCIB200 and pCIB2001, as well as the binary vector pCIB 10 and hygromycin selection derivatives thereof (see, for example, U.S. Pat. No. 5,639,949).

Transformation without the use of *Agrobacterium tumefaciens* circumvents the requirement for T-DNA sequences in the chosen transformation vector and consequently vectors lacking these sequences are utilized in addition to vectors such as the ones described above which contain T-DNA sequences. Transformation techniques that do not rely on *Agrobacterium* include transformation via particle bombardment, protoplast uptake (e.g., PEG and electroporation) and microinjection. The choice of vector depends largely on the preferred selection for the species being transformed. Typical vectors suitable for non-Agrobacterium transformation include pCIB3064, pSOG19, and pSOG35 (see, for example, U.S. Pat. No. 5,639,949).

I. Prescreening of Cultures from Different Genotypes

One embodiment provides a method for increasing the efficiency of transforming plant tissue by preselecting the plant material. For example, mature caryopses can be induced to form highly embryogenic callus cultures (Denchev et al., (1994), *Crop Sci.* 34:1623-1627). Dedifferentiation of caryopses into embryogenic callus cultures can be achieved using numerous basal media with various plant growth hormones. Callus induction from caryopses, young leaf tissue, and portions of seedlings can be achieved using a cytokinin in the growth medium. In one embodiment, production of embryogenic calluses can be obtained in the presence of 2,4-dichlorophenoxyacetic acid (2,4-D) and/or 6-benzylaminopurine (BAP). After multiple transfers onto a fresh medium for callus growth, the regeneration potential of these embryogenic callus cultures is evaluated. Cultures capable of producing about 300 or more plantlets per gram of callus are further propagated and pooled for transformation. Alternatively cultures capable of producing about 200 to about 350 or any number within the range of plantlets can be used. The cultures are then transformed using conventional techniques, preferably incubation with *Agrobacterium*.

J. Transformation and Selection of Callus Cultures and Plants

The embryogenic cultures are infected and co-cultivated with an *Agrobacterium* strain carrying the gene constructs encoding enzymes for PHA production with a selectable marker and/or reporter gene. In one embodiment, genes for the production of PHB (phaA, phaB, and phaC) are used. In another embodiment, *Agrobacterium tumefaciens* strain AGL1 is used. In an alternative embodiment, infection and co-cultivation is performed in the presence of acetosyringone. The cultures can then be selected using one or more of the selection methods described above which are well known to those skilled in the art. In a preferred embodiment, selection occurs by incubating the cultures on a callus growth medium containing bialaphos. In an alternative embodiment, selection can occur in the presence of hygromycin. Resistant calluses are then cultured on a regeneration medium (Somleva, (2006), *Agrobacterium Protocols* (Wang K ed), pp. 65-74, Humana Press; Somleva et al., (2002), *Crop Sci.* 42:2080-2087) containing the preferred selection agent.

IV. Methods of Use

The disclosed transgenic plants can be used to produce PHAs, in particular poly(3-hydroxybutyrate), as well as lignocellulosic biomass. Plants are typically produced by seeding of prepared fields, then harvesting the biomass using conventional hay or grain harvesting equipment. Polymer is extracted by solvent extraction in most cases, and then processed using standard techniques.

The PHB can be used in a variety of applications including packaging products like bottles, bags, wrapping film and other biodegradable devices. PHB may have medical device applications due to its biodegradability, optical activity and isotacticity.

The lignocellulosic biomass materials can be used to produce biofuels such as ethanol (Lee, J., (1997), *J. Biotechnology* 56(1):1-24. By making use of all of the plant material additional value is obtained.

Thus, one embodiment provides plant feedstock or plant material including at least about 1% to about 4% polyhydroxyalkanoate, preferably poly(3-hydroxybutyrate), and lignocellulosic biomass, wherein the plant does not produce storage products such as oils or carbohydrates. Preferably the plant is switchgrass. The PHA and the lignocellulosic biomass can be extracted from the feedstock using conventional methods.

Unless defined otherwise, all technical and scientific terms used herein have the same meanings as commonly understood by one of skill in the art to which the disclosed invention belongs. Publications cited herein and the materials for which they are cited are specifically incorporated by reference.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Those skilled in the art will recognize, or be able to ascertain using no more than routine experimentation, many equivalents to the specific embodiments of the invention described herein. Such equivalents are intended to be encompassed by the following claims.

EXAMPLES

Example 1

Identification of Switchgrass Genotypes with High Regeneration Potential

Materials and Methods

Switchgrass mature caryopses of cv. 'Alamo' were sterilized and plated on MS medium for callus induction according to Denchev et al., (1994), *Crop Sci.* 34:1623-1627). Cultures were grown at 28° C. in the dark and maintained by monthly subcultures. Their embryogenic response was monitored after each subculture. After three months, callus regeneration ability was tested by transferring pre-weighed pieces of callus from each genotype onto MS medium for plant regeneration (Denchev et al., (1994), *Crop Sci.* 34:1623-1627). Cultures were incubated at 28° C. with a 16 h photoperiod (cool white fluorescent bulbs, 80 μmol/m$^2$/s) and transferred onto a fresh regeneration medium after 4 weeks.

Results

The frequency of callus formation was evaluated four weeks after culture initiation. It varied from 36.4% to 77.3% (Table 1). Approximately 5% of the initial explants formed embryogenic callus (Table 1). For maintenance of a specific genotype, callus originating from a single seed was propagated separately.

After propagation for three months, a certain amount of embryogenic callus from each genotype was used for plant regeneration. Plantlets obtained from each genotype after a culture period of two months were counted and calculated per gram fresh weight of callus (Table 2).

TABLE 1

Embryogenic callus formation from switchgrass mature caryopses (MC), cv. Alamo. Data presented are from three independent experiments.

| Callus initiation experiment | Total number of seeds | MC with callus formation | | MC with embryogenic callus | |
|---|---|---|---|---|---|
| | | number | % to total | number | % to total |
| 1 | 1850 | 701 | 37.9 | 104 | 5.6 |
| 2 | 3924 | 1427 | 36.4 | 195 | 5.0 |
| 3 | 1000 | 773 | 77.3 | 47 | 4.7 |

TABLE 2

Regeneration ability of mature caryopsis-derived embryogenic callus cultures from different switchgrass genotypes (our designation), cv. Alamo.

| Alamo genotype | Callus fresh weight [g] | Regeneration ability | |
|---|---|---|---|
| | | # of plants | # of plants/g FW |
| 38 | 0.212 | 496 | 2340 |
| 56 | 0.191 | 66 | 346 |
| 59 | 0.304 | 320 | 1053 |
| 61 | 0.221 | 380 | 1719 |
| 62 | 0.279 | 629 | 2254 |
| 119 | 0.192 | 178 | 927 |
| 136 | 0.173 | 67 | 387 |
| 215 | 0.167 | 77 | 461 |
| 247 | 0.070 | 45 | 643 |

Example 2

Preparation of Multi-Gene Constructs for PHB Synthesis

Multi-Gene Constructs.

pMBXS159. This binary vector contains expression cassettes for the three gene PHB biosynthetic pathway under the control of the rice polyubiquitin 2 (rubi2) promoter (Wang et al., (2000), *Plant Sci.* 156:201-211). The PHB genes chosen for this construct include a hybrid *Pseudomonas oleovorans/Zoogloea ramigera* PHA synthase (Huisman et al., (2001), U.S. Pat. No. 6,316,262) and the thiolase and reductase from *Raistonia eutropha* (Peoples et al., (1989), *J. Biol. Chem.* 264:15293-15297). Each PHA gene is fused to a plastid targeting sequence encoding the signal peptide of the small subunit of rubisco from pea and the first 24 amino acids of the mature protein (Cashmore, (1983), *Genetic Engineering of Plants* (Kosuge T, Meredith C P and Hollaender A eds), pp. 29-38, New York, Plenum Press) as described by Kourtz et al., (2005), *Plant Biotechnol.,* 3:435-447. Plasmid pMBXS159 was constructed using the following multi-step procedure.

i. pMBXS124, pMBXS125, and pMBXS126. These plasmids contain rubi2 and the 3' termination sequence of nopaline synthase (nos) and differ with respect to the restriction sites available for subsequent cloning purposes (Table 3). The rubi2 and nos fragments were isolated from template plasmids pRGL112-1 and pNEB(A) (Kourtz et al., (2007), *Transgenic Res.* 16:759-769), respectively, using standard PCR techniques. The rubi2 and nos fragments were sub-cloned back into pRGL112-1 forming plasmids pMBXS124-126.

ii. pMBXS135. Plasmid pMBXS135 is a pCAMBIA3300 derived vector in which the maize hsp70 intron (U.S. Pat. No. 5,593,874 to Brown et al.) has been placed between the CaMV35S promoter and bar to increase expression of the selectable marker in monocots. The maize hsp70 intron was isolated by PCR from PCR-Ready maize genomic DNA (Bio-Chain, CA) using primers BGNP108 and BGNP109 and inserted between the CaMV35S promoter and bar gene using conventional cloning techniques.

iii. pMBXS154. Cassettes from pMBXS124, pMBXS125, and pMBXS126, containing rubi2 and nos, were sequentially transferred to pMBXS135 to form pMBXS154. Plasmid pMBXS124 was digested with Sma I and Hind III and the rubi2 nos fragment was ligated into pMBXS135 that had been previously digested with Eco RI, treated with the Klenow fragment of DNA polymerase 1, and digested with Hind III, forming intermediary plasmid pMBXS138. The rubi2 nos cassette of pMBXS125 was isolated upon digestion with Bsp EI and Hind III and the resulting fragment was inserted into the equivalent sites of pMBXS138, forming pMBXS140. The rubi2 nos cassette of pMBXS126 was isolated upon digestion with Bsr GI and Hind III and inserted into the equivalent sites of pMBXS140 forming pMBXS154.

iv. pMBXS159. The PHB biosynthetic genes, each modified with the plastid targeting signal from pea (TS), were sequentially inserted into plasmid pMBXS154 using the following multi-step procedure to form pMBXS159. A PCR fragment containing TS-phaC was isolated from pNEB(C) (Table 3) using conventional PCR procedures and inserted into the Avr II and Bam HI sites of pMBXS154 forming plasmid pMBXS156. A fragment containing TS-phaA-nos was isolated by PCR from plasmid pNEB(A) (Kourtz et al., (2007), *Transgenic Res.* 16:759-769) and inserted into plasmid pMBXS156, which had previously been digested with Bsr GI, blunt-ended with Klenow, and digested with Bst BI, to generate pMBXS157. A fragment containing TS-phaB-nos was isolated by PCR from plasmid pNEB(B) (Table 3) and inserted into plasmid pMBXS157 that had been previously digested with Asc I, blunt-ended with Klenow, and digested with Hind III, to form plasmid pMBXS159.

pMBXS155. Plasmid pMBXS155 is a binary vector in which the PHB genes described above are expressed under the control of a maize chlorophyll A/B binding protein promoter (Sullivan et al., (1989), *Mol. Gen. Genet.* 215:431-440). This promoter is equivalent to the cab-m5 promoter described by Becker et al., (1992), *Plant Mol. Biol.* 20:49-60. In pMBXS155, the cab-m5 promoter is fused to the hsp70 intron (U.S. Pat. No. 5,593,874 to Brown et al.) for enhanced expression in monocots. pMBXS155 was constructed using the following multi-step procedure.

i. pMBXS137, pMBXS143 and pMBXS144. These plasmids contain cab-m5, the hsp70 intron, and nos and differ with respect to the restriction sites available for subsequent cloning purposes (Table 3). The fragment containing cab-m5 was amplified from PCR-Ready maize genomic DNA (Bio-Chain, CA) with primers BGNP110 and BGNP111.

ii. pMBXS148. Expression cassettes from plasmids pMBXS137, pMBSX143, and pMBXS144 were sequentially inserted into plant transformation vector pMBXS135 as follows. Plasmid pMBXS137 was digested with Sma I and Hind III and the cab-m5/hsp70 nos fragment was ligated to plasmid pMBXS135 that had been previously digested with Eco RI, treated with Klenow, and digested with Hind III to create pMBXS145. This plasmid was modified by introducing an Eco RI site at the 3' end of nos to generate pMBXS146. The cab-m5/hsp70 nos fragment of pMBXS143 was isolated with an Eco RI and Hind III digest and cloned into the Eco RI and Hind III sites of pMBXS146 to generate pMBXS147. The third cab-m5/hsp70 nos cassette was isolated from pMBXS144 by digestion with Bsr GI and Hind III was cloned into the Bsr GI and Hind III sites of pMBXS147 to create pMBXS148.

iii. pMBXS155. A fragment containing TS-phaC was isolated from pNEB(C) using conventional PCR procedures and inserted into the Avr II and Bam HI sites of pMBXS148 to form plasmid pMBXS151. Similarly, a fragment containing TS-phaA-nos was isolated by PCR from plasmid pNEB(A) (Kourtz et al., (2007), *Transgenic Res.* 16:759-769) and inserted into plasmid pMBXS151, which had previously been digested with Bsr GI, blunt-ended with Klenow, and digested with Bst BI, to generate pMBXS153. Insertion of the PHB genes was completed by isolating a fragment containing TS-phaB from plasmid pNEB(B) and inserting at the Pac I and Asc I sites of pMBXS153 to create pMBXS155.

TABLE 3

Plasmids and primers.

| | Relevant Characteristics | Reference |
|---|---|---|
| Plasmids & Primers | | |
| pRGL112-1 | pUC19-based vector with rubi2 fused to GUS; source of rubi2 for subsequent cloning efforts | (Wang et al., 2000, Plant Sci. 156: 201-211) |
| pNEB(A) | pNEB193 derivative (New England Biolabs), contains 35S-C4PPDK promoter, TS, phaA, nos | (Kourtz et al., 2007, Transgenic Res. 16: 759-769) |
| pMBX124 | pUC19-based vector; contains Sma I-rubi2 & Avr II-Bam HI-nos-Bsp EI-Hind III cassettes | This study |
| pMBX125 | pUC19-based vector; contains Bsp EI-rubi2 & Bst BI-nos-Bsr GI-Hind III cassettes | This study |
| pMBX126 | pUC19-based vector; contains Bsr GI-rubi2 & Asc I-nos-Hind III cassettes | This study |
| pCAM3300 | pCAMBIA3300 binary vector; contains CaMV35S bar expression cassette conferring resistance to bialaphos | CAMBIA |

TABLE 3-continued

Plasmids and primers.

| | Relevant Characteristics | Reference |
|---|---|---|
| pMBXS135 | modified pCAMBIA3300 binary vector; contains CaMV35S hsp70 bar cassette to increase bar expression | This study |
| pMBXS138 | pMBXS135 with rubi2-Avr II-Bam HI-nos-Bsp EI-Hind III | This study |
| pMBXS140 | pMBXS135 with rubi2-Avr II-Bam HI-nos-Bsp EI-rubi2-Bst BI-nos-Bsr GI-Hind III | This study |
| pMBXS154 | pMBXS135 with rubi2-Avr II-Bam HI-nos-Bsp EI-rubi2-Bst BI-nos-Bsr GI-rubi2-Asc I-nos-Hind III | This study |
| pNEB(C) | Similar to pNEB(A); contains 35S-C4PPDK promoter, TS, phaC, nos | This study |
| pMBXS156 | pMBXS135 with rubi2-Avr II-TS-phaC-Bam HI-nos-Bsp EI-rubi2-Bst BI-nos-Bsr GI-rubi2-Asc I-nos-Hind III | This study |
| pMBXS157 | pMBXS135 with rubi2-Avr II-TS-phaC-Bam HI-nos-Bsp EI-rubi2-Bst BI-TS-phaA-nos-rubi2-Asc I-nos-Hind III | This study |
| pNEB(B) | Similar to pNEB(A); contains 35S-C4PPDK promoter, TS, phaB, nos | This study |
| pMBXS159 | pMBXS135 with rubi2-Avr II-TS-phaC-Bam HI-nos-Bsp EI-rubi2-Bst BI-TS-phaA-nos-rubi2-TS-phaB-nos-Hind III | This study |
| pMBXS137 | pNEB193-based vector with Sma I-cab-m5/hsp70 & Avr II-Bam HI-nos-Hind III cassettes | This study |
| pMBXS143 | pNEB193-based vector with Eco RI-cab-m5/hsp70 & Bst BI-nos-Bsr GI-Hind III cassettes | This study |
| pMBXS144 | pNEB193-based vector; contains Bsr GI-cab-m5/hsp70 & Pac I, Asc I-nos -Hind III cassettes | This study |
| pMBXS145 | pMBX135 with cab-m5/hsp70-Avr II-Bam HI-nos-Hind III | This study |
| pMBXS146 | pMBX135 with cab-m5/hsp70-Avr II-Bam HI-nos-Eco RI-Hind III | This study |
| pMIBXS147 | pMBX135 with cab-m5/hsp70-Avr II-Bam HI-nos-Eco RI-cab-m5/hsp70-Bst BI-nos-Bsr GI-Hind III | This study |
| pMBXS148 | pMBX135 with cab-m5/hsp70-Avr II-Bam HI-nos-Eco RI-cab-m5/hsp70-Bst BI-nos-Bsr GI-cab-mS/hsp70-Pac I-Asc I-nos-Hind III | This study |
| pMBXS151 | pMBX135 with cab-m5/hsp70-Avr II-TS-phaC-Bam HI-nos-Eco RI-cab-m5/hsp70-Bst BI-nos-Bsr GI-cab-m5/hsp70-Pac I-Asc I-nos-Hind III | This study |
| pMBXS153 | pMBX135 with cab-m5/hsp70-Avr II-TS-phaC-Bam Hi-nos-Eco RI-cab-m5/hsp70-Bst BI-TS-phaA-nos-cab-m5/hsp70-Pac I-Asc I-nos-Hind III | This study |
| pMBXS155 | pMBX135 with cab-m5/hsp70-Avr II-TS-phaC-Bam HI-nos-Eco RI-cab-m5/hsp70-Bst BI-TS-phaA-nos-cab-m5/hsp70-Pac I-TS-phaB-Asc I-nos-Hind III | This study |
| Primers | | |
| BGNP108 | 5' *AGATCTACCGTCTTCGGTACGCGCTC* 3' (SEQ ID NO: 1) | This study |
| BGNP109 | 5' *CCATGGCCGCTTGGTATCTGCATTAC* 3' (SEQ ID NO: 2) | This study |
| BGNP110 | 5' *GAA TTCACGGAAGATCCAGGT* 3' (SEQ ID NO: 3) | This study |

TABLE 3-continued

Plasmids and primers.

| | Relevant Characteristics | Reference |
|---|---|---|
| BGNP111 | 5' *AGATCTT*GCTGAAGCTGAGCGTGAAAG 3' (SEQ ID NO: 4) | This study |
| bar_fwd | 5' GCACCATCGTCAACCACTACATCG 3' (SEQ ID NO: 5) | This study |
| bar_rev | 5' TCATGCCAGTTCCCGTGCTTG 3' (SEQ ID NO: 6) | This study |
| phaA_fwd | 5' ATCATCGCAAGACCGGCAACAG 3' (SEQ ID NO: 7) | This study |
| phaA_rev | 5' TACAAGAGCTATGCCAACGC 3' (SEQ ID NO: 8) | This study |
| phaB_fwd | 5' GCAAGACCGGCAACAGGATTCA 3' (SEQ ID NO: 9) | This study |
| phaB_rev | 5' TCGGCGAGGTTGATGTGCTGAT 3' (SEQ ID NO: 10) | This study |
| phaC_fwd | 5' GTAACATAGATGACACCGCG 3' (SEQ ID NO: 11) | This study |
| phaC_rev | 5' GAAACAGCCTGAAAGTGCC 3' (SEQ ID NO: 12) | This study |
| phaC_fwd1 | 5' GCTGGGCGATATCAACAA 3' (SEQ ID NO: 13) | This study |
| phaC_rev1 | 5' GCACATAGTTCCATACCAGGTC 3' (SEQ ID NO: 14) | This study |
| ActA | 5' CACTGGAATGGTCAAGGATG 3' (SEQ ID NO: 15) | (Okubara et al, 2002, Theor. App Genet. 106: 74-83 |
| ActB | 5' CTCCATGTCATCCCAGTTG 3' (SEQ ID NO: 16) | (Okubara et al., 2002, Theor. App Genet. 106: 74-83 |

*a*Abbreviations: GUS, β-glucuronidase gene; cab-m5/hsp70, cab-m5 promoter from maize fused to the hsp70 intron from maize; TS, plastid targeting sequence; phaA, gene encoding thiolase; phaB, gene encoding reductase; phaC, gene encoding synthase; nos, 3' terminator from nopaline synthase gene; e35S promoter, double enhanced version of the 35S promoter from cauliflower mosaic virus. Relevant restriction sites mentioned in the text are indicated in bold.

Example 3

Transformation of Switchgrass Cultures with Multi-Gene Constructs for PHB Synthesis and Selection of Transgenic Plants Materials and Methods Cultures capable of producing more than 300 plantlets per gram of callus were used for *Agrobacterium*-mediated transformation. Embryogenic cultures were infected and co-cultivated with *Agrobacterium tumefaciens* strain AGL1 carrying the binary vector pMBXS155 or pMBXS159 in the presence of 100 μM of acetosyringone as described by Somleva, (2006); *Agrobacterium Protocols* (Wang K ed), pp. 65-74, Humana Press; Somleva et al., (2002), *Crop Sci.* 42:2080-2087. Cultures were selected with 10 mg/L bialaphos for 2-4 months. Resistant calluses were transferred to a regeneration medium containing 10 mg/L bialaphos (Somleva, (2006); *Agrobacterium Protocols* (Wang K ed), pp. 65-74, Humana Press; Somleva et al., (2002), *Crop Sci.* 42:2080-2087). Cultures were incubated at 28° C. with a 16 h photoperiod (cool white fluorescent bulbs, 80 μmol/m²/s) for 4 to 6 weeks with biweekly subcultures. The resultant plantlets were treated with the herbicide Basta™ as described by (Somleva, (2006); *Agrobacterium Protocols* (Wang K ed), pp. 65-74, Humana Press; Somleva et al., (2002), *Crop Sci.* 42:2080-2087). Transgenic and control plants were grown in a greenhouse at 28° C. with supplemental lighting (16 hour photoperiod, Na halide lamps).

Results

Two different promoters for expression of the PHB biosynthetic pathway in switchgrass were compared: the strong constitutive promoter of the rice ubiquitin 2 gene (Wang et al., (2000), *Plant Sci.* 156:201-211) and the cab-m5 light inducible promoter of the chlorophyll A/B binding protein in maize (Becker et al., (1992); *Plant Mol. Biol.* 20:49-60, Sullivan et al., (1989), *Mol. Gen. Genet.* 215:431-440) fused to the hsp70 intron (Brown et al., (1997), U.S. Pat. No. 5,593,874). These promoters were assembled into expression cassettes with PHB pathway genes that had been previously appended at the 5' end with a DNA sequence encoding a plastid targeting signal (Kourtz et al., (2005), *Plant Biotechnol.* 3:435-447) forming the cab-m5 promoter construct pMBXS155 and the rubi2 promoter construct pMBXS159. Highly embryogenic callus cultures were inoculated with *Agrobacterium tumefaciens* strain AGL1 (Lazo et al., (1991), *Bio/Technol.* 9:963-967) harboring pMBXS159 or pMBXS155 and transformed cultures were selected for functional expression of the bar gene imparting resistance to bialaphos. Regenerated plantlets were further screened by treatment with the herbicide Basta™.

Example 4

PHB Production in Switchgrass Leaves

Materials and Methods

To measure PHB content, leaf tissues (20-80 mg) from primary transformants in tissue culture were collected, lyophilized and prepared for analysis by gas chromatography/mass spectroscopy (GC/MS) using a previously described simultaneous extraction and butanolysis procedure (Kourtz et al., (2007), *Transgenic Res.* 16:759-769).

For screening of PHB producing lines grown under greenhouse conditions, samples from mature leaves adjacent to the node at the base of the stem and younger still developing leaves at the top of the stem of plants grown in soil for two months were analyzed. For spatial distribution analysis, whole tillers (the basic units of harvested switchgrass biomass, (Moser et al., (2007), *The Science of Grassland Agriculture* (Barnes R F, Nelson C J, Moore K J and Collins M eds), pp. 15-35, Ames, Iowa, Blackwell Publishing) at a vegetative growth stage and at a reproductive stage were used. The following tissues were collected: nodes, internodes, leaf sheaths, leaf blades, and panicles (from flowering tillers). Samples were prepared as described above and analyzed in selected ion monitoring mode using an Agilent 5973 GC/MS equipped with a DB-225MS column and guard (Moser et al., (2007), *The Science of Grassland Agriculture* (Barnes R F, Nelson C J, Moore K J and Collins M eds), pp. 15-35, Ames, Iowa, Blackwell Publishing).

Results

Figure 2A:
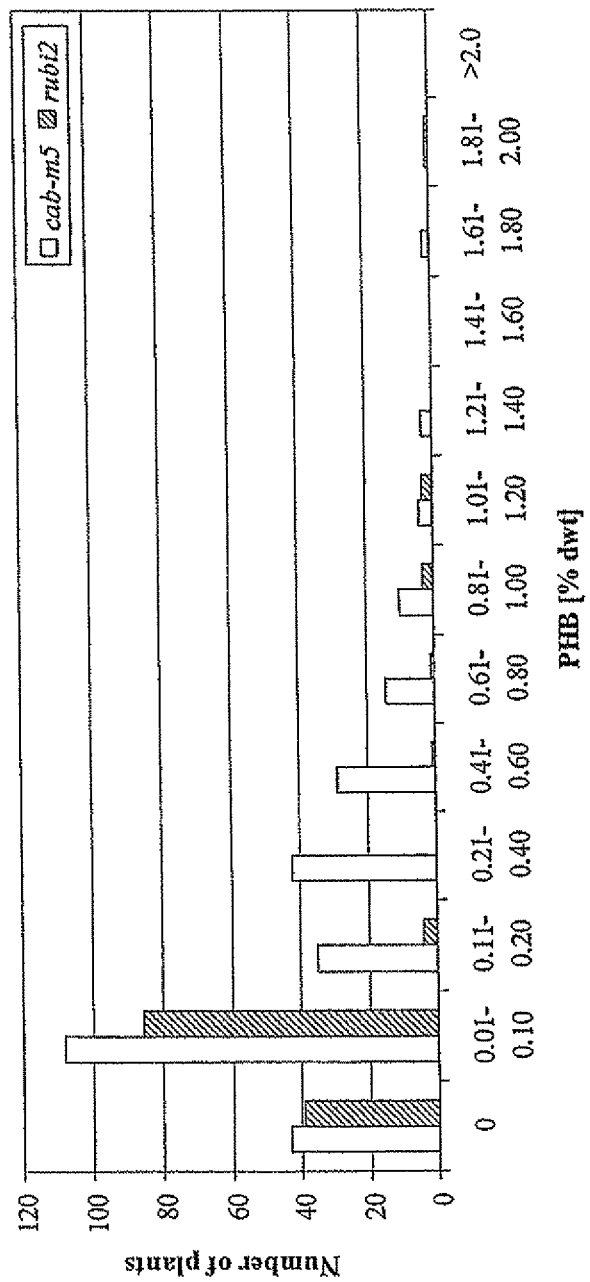
FIG. 2a is a bar graph of number of plants versus percent PHB dry weight (dwt) in leaf tissues harvested from plantlets transformed with pMBXS155 (cab-m5 promoter construct (white shaded bars)) and pMBXS159 (rubi2 promoter construct (hatched bars), and grown in tissue culture before transfer to soil.

Polymer content in regenerated plantlets grown under in vitro conditions was measured in 428 PCR positive plants prior to transfer to soil (FIG. 2a). Polymer content is expressed as % PHB per unit dry weight (dwt) of plant tissue. The majority of regenerated plantlets accumulated detectable PHB amounts less than 0.10% PHB per unit dry weight (dwt) (37% and 62% for the cab-m5 and rubi2 constructs, respectively). The remaining plants possessed a range of polymer levels up to 1.82% dwt PHB.

Figure 2B:
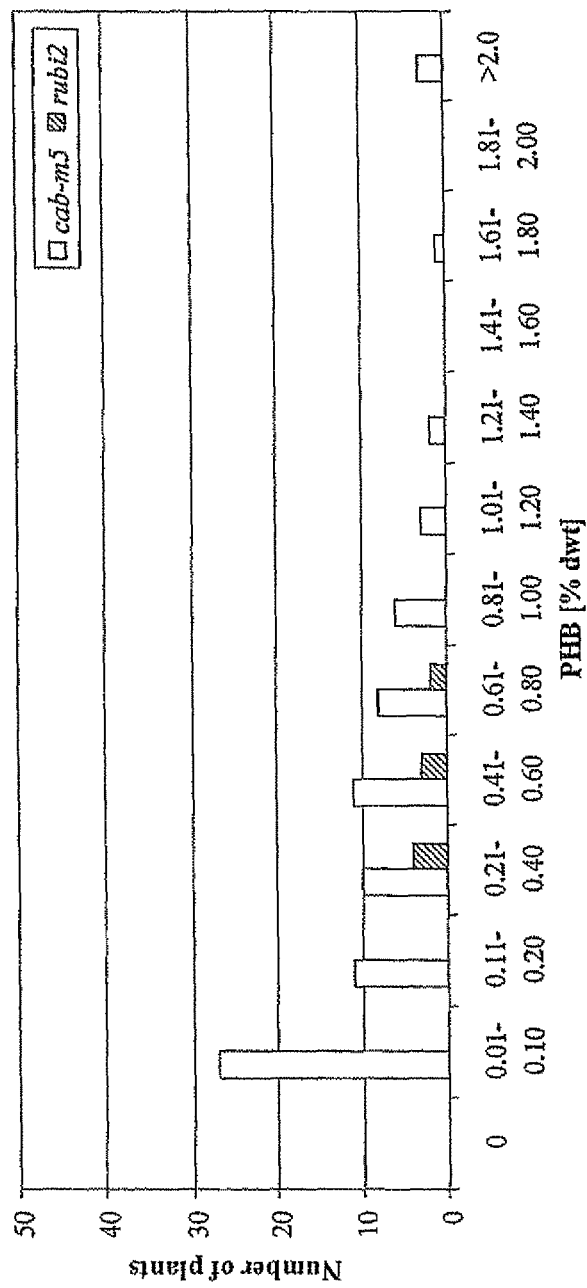
FIG. 2b is a bar graph of number of plants versus percent PHB dwt in the upper part of the blades of mature leaves adjacent to the basal stem node of adult plants transformed with pMBXS155 (cab-m5 promoter construct, white bars) and pMBXS159 (rubi2 promoter construct, (hatched bars) analyzed after two months growth in a greenhouse.

Plants containing greater than or equal to 0.30% dwt PHB (82 cab-m5 and 9 rubi2 plants) were transferred to soil for further analysis. After two months of growth, samples from mature leaves adjacent to the node at the base of the tiller as well as fully expanded, still developing young leaves at the top node, were analyzed for polymer production (FIG. 2b, c). In about 30% of the plants transformed with pMBXS155, the PHB content in mature leaves was similar to values measured under in vitro conditions. About 12% of the plants showed a two- to five-fold increase in polymer levels with the highest producing plant yielding 2.56% dwt PHB. The polymer content in mature leaves of all nine pMBXS159 plants was two to four times lower than the levels produced under in vitro conditions with up to 0.79% dwt PHB.

Figure 2C:
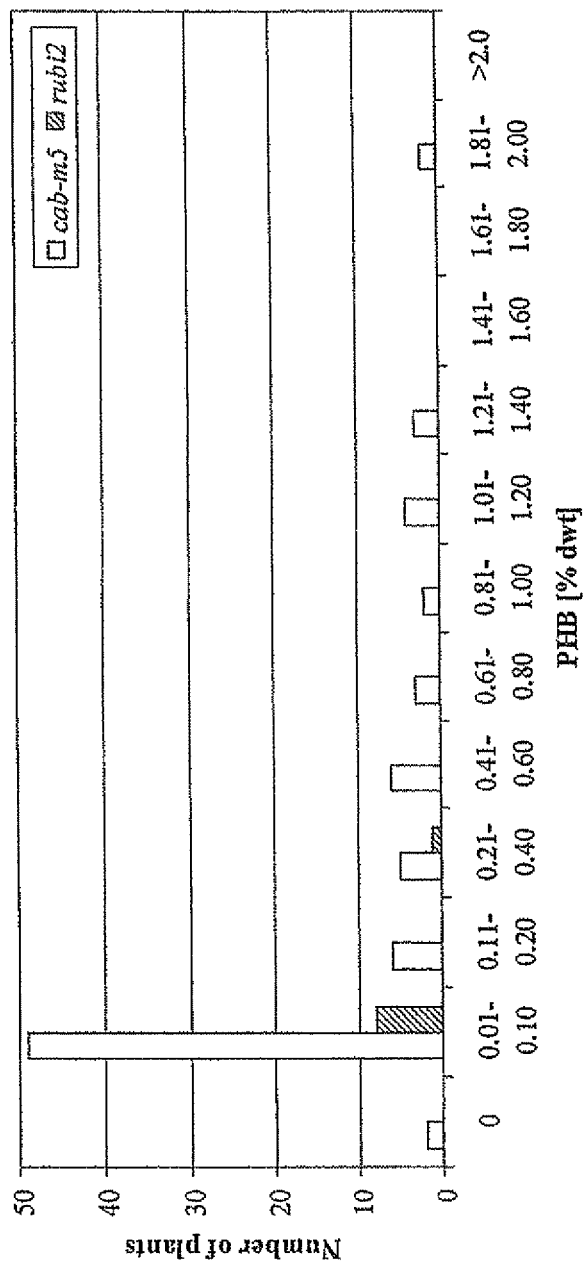
FIG. 2c is a bar graph of number of plants versus percent PHB dwt from young developing leaves at the top of the stem of adult plants transformed with pMBXS155 (cab-m5 promoter construct, white bars) and pMBXS159 (rubi2 promoter construct (hatched bars), analyzed after two months growth in a greenhouse.

In developing leaves of plants transformed with pMBXS155, approximately 60% of plants possessed less than 0.10% dwt PHB (FIG. 2c). The highest producer contained 1.99% dwt PHB. The polymer levels in plants transformed with pMBXS159 were significantly lower, with up to 0.23% dwt detected in developing leaves.

PHB content was also determined in mature and developing leaves of new tillers of 31 plants transformed with pMBXS155 that were grown for two months after harvesting and repotting (second generation tillers). PHB production in 20 of these plants was equal to or higher (up to 3.55% dwt) than levels observed in the first generation tillers. In a similar analysis of seven pMBXS159 plants, none of the second generation tillers had a higher PHB content.

In total, nineteen plants, representing 6.5% of the population of cab-m5 plants analyzed in this study (291 plants), accumulated from 1.00% to 3.55% dwt PHB in fully developed mature leaves.

Example 5

Molecular Analyses

Materials and Methods

PCR

The presence of transgenes in plantlets regenerated from bialaphos-resistant calluses was detected in total nucleic acid extracts obtained from leaf tissues of in vitro grown plantlets with 3 to 4 leaves using the REDExtract Plant PCR Kit (Sigma-Aldrich). Sequences of primers specific for the coding regions of transgenes are listed in Table 3. The primer pairs were as follows: phaA, primers phaA_fwd and phaA_rev; phaB, primers phaB_fwd and phaB_rev; phaC, primers phaC_fwd and phaC_rev; bar, primers bar_fwd and bar_rev. PCR conditions for all amplifications were as follows: 96° C. for 30 sec (1 cycle); 95° C. for 1 min, 57° C. for 1 min, 72° C. for 1 min (35 cycles); 72° C. extension for 15 min.

Southern Blot Hybridizations

Switchgrass genomic DNA was isolated from young leaf tissues and after complete digestion with SacI was separated and blotted as described previously (Somleva et al., (2002), *Crop Sci.* 42:2080-2087). Hybridizations were performed at 62° C. using fragments of the coding regions of the bar (394 bp) and phaB (578 bp) genes as probes. The digoxigenin-labeled probes were generated by PCR amplification (PCR DIG Probe Synthesis Kit, Roche) using the primers in Table 3 and the PCR conditions described above. Digoxigenin-hybridized fragments were detected with the DIG Luminescent Detection Kit (Roche) using CSPD as a chemiluminescent substrate according to the manufacturer's protocol.

Results

The presence of the transgenes was confirmed by PCR. Approximately 9% of the regenerated plants were found to be non-transformed escapes. Transformation efficiencies, defined as the number of PCR positive plants recovered per inoculated explant, varied from 0 to 93% depending on the genotype and the gene construct utilized in the transformation (Table 4).

Southern hybridizations were performed on 48 PCR positive plants regenerated from 17 bialaphos-resistant callus lines transformed with pMBXS155 (FIG. 1). Twenty-seven independent transformation events were identified by their unique integration patterns. The T-DNA copy number detected in these lines ranged from 1 to 9. About 50% of the independent transformants analyzed had one (6 events) or two (8 events) gene copies. Thirteen transformation events were found to have multiple (3-9) T-DNA copies. In some lines, differences in the number of bands detected with the phaB and bar gene probes were observed suggesting possible rearrangements of the T-DNA. The integration patterns of other lines suggest the presence of tandem repeats. Interestingly, some of these plants are among the best PHB producers identified in this study.

TABLE 4

Transformation response of mature caryopsis-derived embryogenic callus cultures from various switchgrass genotypes (our designation), cv. Alamo.

| Alamo genotype | cab-m5 promoter construct | | | rubi2 promoter construct | | |
|---|---|---|---|---|---|---|
| | # of calluses inoculated[a] | # of calluses transformed[b] | # of plantlets[c] | # of calluses inoculated[d] | # of calluses transformed[b] | # of plantlets[c] |
| 56 | 258 | 83 | 240 | 113 | 28 | 104 |
| 92 | 128 | 2 | 10 | 49 | 0 | 0 |
| 119 | 43 | 1 | 3 | 37 | 1 | 3 |
| 136 | 201 | 4 | 14 | 71 | 12 | 22 |
| 215 | 113 | 13 | 25 | 124 | 6 | 5 |
| 247 | 51 | 5 | 13 | 64 | 7 | 21 |
| Total: | 794 | 108 | 305 | 458 | 54 | 155 |

[a]callus cultures inoculated with *A. tumefaciens* AGL1/pMBXS155;
[b]bialaphos-resistant calluses producing transgenic plantlets;
[c]transgenic plantlets carrying all four transgenes as confirmed by PCR;
[d]callus cultures inoculated with AGL1/pMBXS159.

Example 6

PHB Formation in Switchgrass Leaf Cells

Materials and Methods

The subcellular localization of granules in switchgrass leaves was visualized by transmission electron microscopy as follows. Plants were placed in a dark room for 22 h prior to sampling for TEM to allow degradation of starch. Segments from the basal leaf of tillers with four nodes were harvested 6 cm below the tip of both wild-type and PHB producing plants. Polymer contents in leaf segments were measured by GC/MS. Small pieces of leaf were fixed in 2% paraformaldehyde and 2% glutaraldehyde in sodium cacodylate buffer (50 mM, pH 7.0) for 6 h at 22° C. Samples were post-fixed in 1% osmium tetroxide in the same buffer for 2 h, dehydrated in a graded series of acetone, and embedded in Spurr's epoxy resin. Transverse sections (60 nm thick) were stained with uranyl acetate and lead citrate and observed in a JEOL JSM-100s TEM (JEOL USA, Inc., Peabody, Mass.) operated at 80 kV.

Results

Analysis by TEM demonstrated that granules were located in the chloroplasts of leaves from plants transformed with the pMBXS155 gene construct. The polymer content in the leaf region sampled for TEM was 1.60% dwt. Bundlesheath chloroplast from a wild-type plant contained large starch granules. PHB granules were observed primarily in the chloroplasts of the bundle sheath cells and occasionally in the mesophyll cells. In both cell types, granule formation was often co-localized with plastoglobules. In samples from wild-type leaves, no granules of PHB were observed. Despite incubation of plants in the dark for 22 hours prior to sampling, starch granules were still visible in the chloroplasts of the bundle sheath cells of wild-type plants but were absent in the chloroplasts of PHB producers.

Example 7

Effect of PHB Production on Plant Growth and Development

All of the plantlets obtained from callus transformed with pMBXS155 grew normally in tissue culture. A few plants regenerated from cultures constitutively expressing the pha genes showed some phenotypic changes under in vitro conditions. Some soil-grown plants that accumulated more than 2% dwt PHB in mature leaves were observed to have slight chlorosis and growth reduction without drastic changes in plant development. However, normally growing plants containing similar amounts of PHB were also obtained. The ability to generate fertile PHB-producing plants phenotypically similar to wild-type plants suggests that product accumulation at these levels is well tolerated by switchgrass plants. Plants from switchgrass genotype 56 after two months in the greenhouse contained 2.27% dwt PHB in a sample from a mature leaf adjacent to the basal node. Plants from genotype 215 after two months in the greenhouse transformed with the cab-m5 gene construct contained 2.52% dwt PHB in a sample from a mature leaf adjacent to the basal node.

Example 8

Polymer Accumulation in Whole Plants

Materials and Methods

The spatial distribution of PHB was examined in leaf blades and stem tissues (nodes, internodes, leaf sheaths, panicles) of transgenic plants grown under greenhouse conditions. Tillers at both a vegetative stage (3-4 visible nodes) or at a reproductive stage (4-5 nodes with developing panicles) were harvested and analyzed. Since PHB was not detected in roots during preliminary experiments, root samples were not included in this experiment. Four cab-m5 lines, representing three different groups of plants with regard to previously measured leaf polymer content in in vitro and soil grown plants were analyzed: a low-producing line containing 0.05% (in vitro) and 0.06% (mature leaf) dwt PHB; a medium producer I with 0.50% and 0.44% dwt, respectively; a medium producer II containing 1.16% and 0.72% dwt; and a high producer containing 0.46% and 2.28% dwt PHB.

Results

Figure 3A:
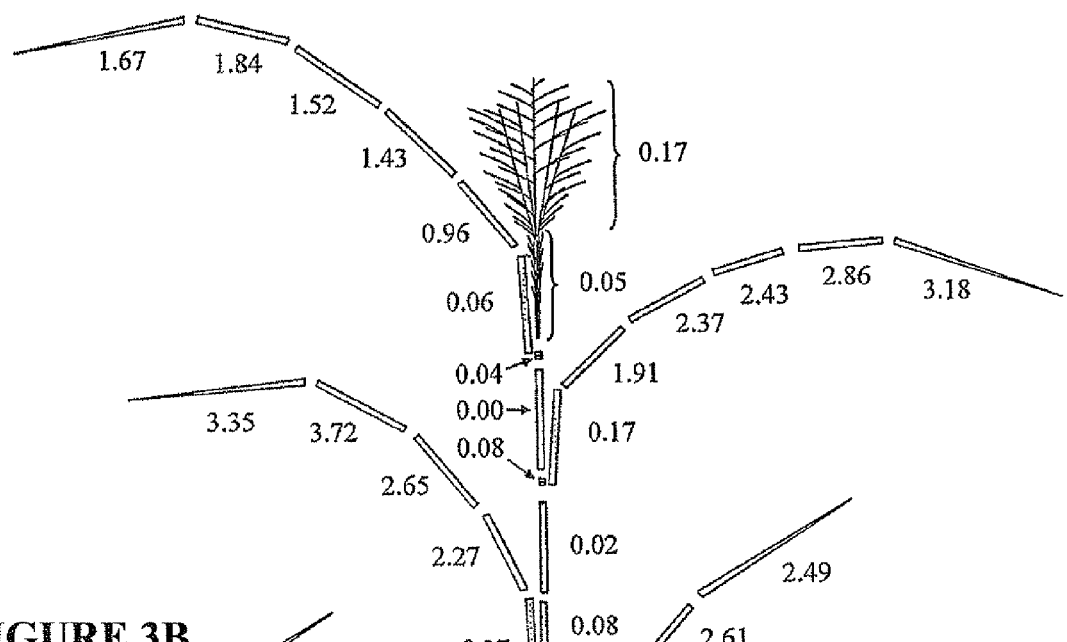
FIG. 3a is a diagram of the spatial distribution of PHB in a reproductive tiller from a high producer. Sections from the nodes, internodes, leaf sheaths, leaf blades, and the panicle were cut and the length and dry weight of each sample was recorded. Numbers indicate the PHB content (% dwt) of each sample as measured by GC/MS.
Figure 3B:
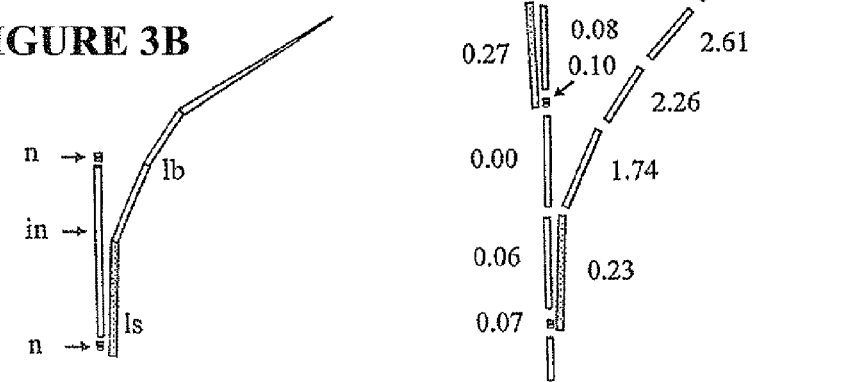
FIG. 3b shows a scheme of the basic unit (phytomer) of the grass plant. n, node; in, internode; ls, leaf sheath; lb, leaf blade.

Examination of the spatial distribution of polymer in switchgrass demonstrated that PHB accumulation was consistently higher in fully developed mature plant tissues in the base of the tiller than the tissues at the top of the tiller. In a single leaf, polymer contents increased from the base to the tip and mature leaves yielded more polymer than young developing leaves. The polymer distribution in a reproductive tiller from a high producer is shown in FIGS. 3a and 3b. The highest polymer content was measured in the oldest leaf regions within 30 cm of the tip. These leaf parts accumulated significant amounts of polymer with up to 3.72% dwt. Stem tissues were found to contain much lower polymer levels than the leaf blades (0-0.17% dwt). Similar PHB distribution patterns were observed in the other lines producing lower amounts of polymer in soil (Table 5). Reproductive tillers of each of the lines analyzed contained more polymer than vegetative tillers suggesting a similar development-dependent pattern of product accumulation despite significant differences in the absolute PHB values among the lines. Biomass partitioning data (Table 5) revealed that stem tissues primarily accounted for the increased dry weight of flowering tillers. Leaf:stem ratios of 0.9-1.1 in vegetative tillers dropped to 0.5-0.7 in tillers at a reproductive stage in the low and the two medium producers, while flowering tillers from the high producer maintained a relatively high (1.1) leaf:stem ratio. The higher polymer levels in reproductive tillers combined with insignificant changes in leaf biomass at this developmental stage (0-28%) suggest that PHB synthesis continues during plant maturation.

TABLE 5

PHB production and biomass accumulation in leaf and stem tissues of vegetative and reproductive tillers from switchgrass lines transformed with the cab-m5 promoter construct.

| Transgenic line | Sample description | Vegetative stage | | Reproductive stage | |
| --- | --- | --- | --- | --- | --- |
| | | dwt [mg] | PHB % dwt | dwt [mg] | PHB % dwt |
| Low producer | Whole tiller | 1918 | 0.01 | 2667 | 0.03 |
| | Leaf blade | 918 | 0.01 | 1063 | 0.08 |
| | Leaf sheath | 429 | 0 | 373 | 0 |
| | Internode | 482 | 0 | 768 | 0 |
| | Node | 89 | 0 | 121 | 0 |
| | Panicle | — | — | 343 | 0 |
| Medium producer I | Whole tiller | 1848 | 0.12 | 2880 | 0.20 |
| | Leaf blade | 955 | 0.23 | 1225 | 0.46 |
| | Leaf sheath | 329 | 0 | 553 | 0.01 |
| | Internode | 470 | 0 | 777 | 0 |
| | Node | 94 | 0 | 160 | 0 |
| | Panicle | — | — | 202 | 0 |
| Medium producer II | Whole tiller | 2287 | 0.18 | 3458 | 0.38 |
| | Leaf blade | 1165 | 0.36 | 1171 | 1.09 |
| | Leaf sheath | 318 | 0 | 468 | 0.07 |
| | Internode | 689 | 0 | 1007 | 0.01 |
| | Node | 97 | 0 | 138 | 0 |
| | Panicle | — | — | 682 | 0.02 |
| High producer | Whole tiller | 1250 | 0.89 | 1165 | 1.23 |
| | Leaf blade | 673 | 1.62 | 606 | 2.18 |
| | Leaf sheath | 214 | 0.06 | 210 | 0.14 |
| | Internode | 303 | 0.01 | 238 | 0.07 |
| | Node | 60 | 0.05 | 56 | 0.08 |
| | Panicle | — | — | 56 | 0.39 |

Example 9

PHB Production in the Progeny of Primary Transformants

Materials and Methods

Due to the high self-incompatibility of switchgrass, $T_1$ seeds were obtained from cross pollination of transgenic plants from different Alamo genotypes used as both male and female parents as described by (Somleva et al., (2002), Crop Sci. 42:2080-2087). Dry seeds from individual crosses were germinated and the resultant seedlings were transferred to soil. Their response to the herbicide Basta™ was tested (Somleva et al., (2002), *Crop Sci.* 42:2080-2087) and the presence of the transgenes in the tolerant plants was confirmed by PCR following the procedure for identification of primary transformants (see Example 5). The segregation ratios were analyzed by the $\chi^2$ test at P=0.05. Transgenic $T_1$ plants (10-19 per cross) were grown in the greenhouse for further analyses. PHB contents were determined by GC/MS (Kourtz et al., (2007), *Transgenic Res.* 16:759-769) in leaf samples collected from $T_1$ plants at the developmental stages used for analyses of the parent $T_0$ plants in tissue culture and soil.

Results

The segregation ratios for Basta™ tolerance/susceptibility of $T_1$ plants from 5 reciprocal crosses between transgenic plants are shown in Table 6. All of the herbicide tolerant seedlings possessed the pha genes as confirmed by PCR. PHB production in the progeny was analyzed in leaf tissues collected from transgenic seedlings at a growth stage comparable to the stage previously used for analysis of the parent plants in tissue culture. Polymer content in individual $T_1$ plants varied from 0% to 1.82% dwt. Plants accumulating PHB at similar or significantly higher levels (up to 155-fold increase) than the parent lines were identified in the offspring obtained from each cross (Table 6). These results indicated that the pha genes were sexually transmitted through both female and male gametes to the next generation.

Figure 4A:
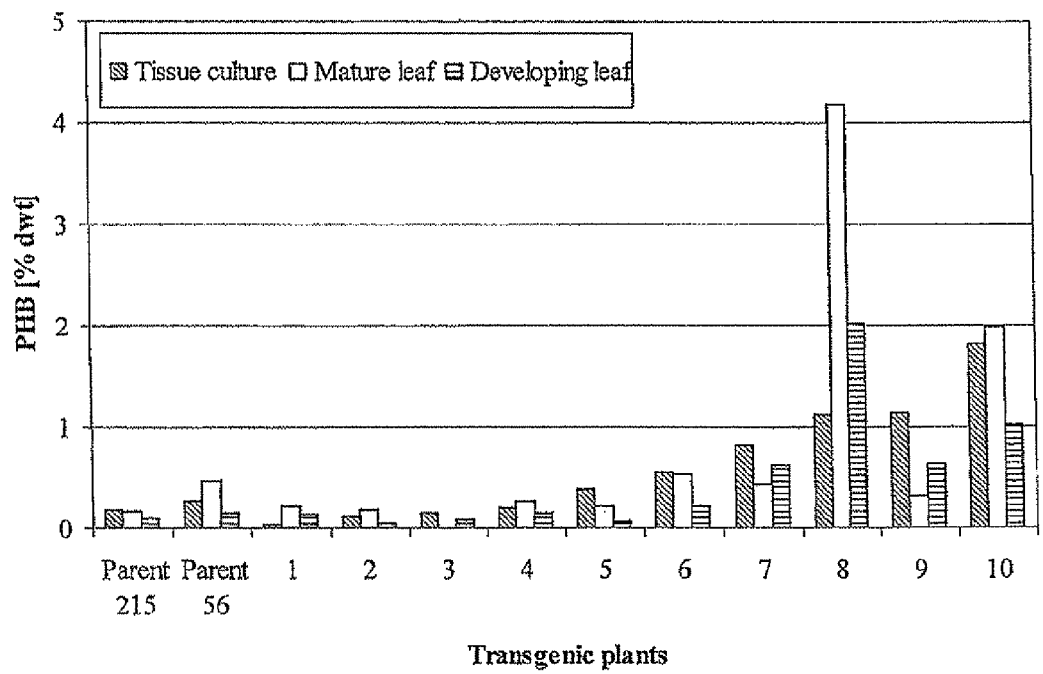
FIG. 4a is a bar graph of percent PHB (dry weight) in $T_0$ plants and their progeny obtained from controlled crosses between two low producers from genotypes 215 and 56.
Figure 4B:
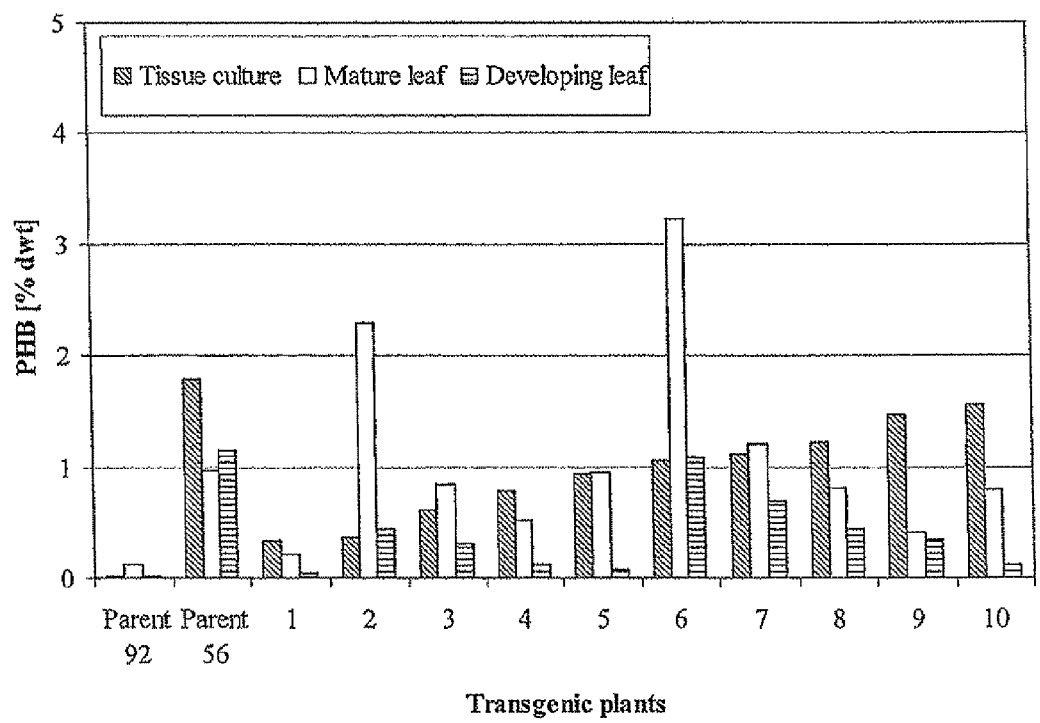
FIG. 4b is a bar graph of percent PHB (dry weight) in $T_0$ plants and their progeny obtained from a cross between the parent lines that include a low producer and a medium producer from genotypes 92 and 56, respectively. Numbers 1-10 indicate individual $T_1$ plants.

PHB content was also measured in mature and developing leaves from $T_1$ plants grown in the greenhouse for two months. Changes in polymer production were found to have patterns similar to those observed in the primary transformants after transfer to soil. For example, in the progeny of a cross between low producers (cross 1 in Table 6), PHB contents in mature leaves were similar to the contents at the seedling stage in 5 of the 10 $T_1$ plants, reduced in 3 plants, and 4-5 times higher (up to 4.19% dwt) in 2 plants (FIG. 4a). Polymer levels in the majority of the $T_1$ plants obtained from cross 2 were lower in the mature leaves compared to the seedlings but 2 plants were found to accumulate 3 to 6-fold more PHB during their growth in the greenhouse ($T_1$ plants 2 and 6, FIG. 4).

TABLE 6

Segregation analysis and PHB production in the $T_1$ progeny obtained from controlled crosses between $T_0$ plants. The $\chi^2$ test is based on the expected segregation ratio of 3:1. PHB contents were measured by GC/MS in leaf tissues from seedlings at a growth stage similar to the stage of the parent plants in tissue culture.

| | | | $T_1$ plants assayed for Basta™ tolerance | | | | PHB content [% dwt] | | | | | |
| --- | --- | --- | --- | --- | --- | --- | --- | --- | --- | --- | --- | --- |
| | Total | No. | | | Ratio | | $T_0$ plants | | $T_1$ plants | | | |
| Cross | number of seeds | of $T_1$ plants | Tolerant | Sensitive | T:S | $\chi^2$ | Parent1 | Parent2 | Range | Mean | Median | SD |
| 1 | 515 | 489 | 372 | 117 | 3.2:1 | 0.30 | 0.18 | 0.26 | 0-1.82 | 0.06 | 0.01 | 0.17 |
| 2 | 171 | 159 | 117 | 42 | 2.8:1 | 0.17 | 1.79 | 0.01 | 0-1.55 | 0.32 | 0.20 | 0.39 |
| 3 | 178 | 154 | 117 | 37 | 3.2:1 | 0.08 | 0.44 | 0.39 | 0-1.60 | 0.17 | 0.05 | 0.28 |

TABLE 6-continued

Segregation analysis and PHB production in the $T_1$ progeny obtained from controlled crosses between $T_0$ plants. The $\chi^2$ test is based on the expected segregation ratio of 3:1. PHB contents were measured by GC/MS in leaf tissues from seedlings at a growth stage similar to the stage of the parent plants in tissue culture.

| Cross | Total number of seeds | No. of $T_1$ plants | $T_1$ plants assayed for Basta™ tolerance Tolerant | $T_1$ plants assayed for Basta™ tolerance Sensitive | Ratio T:S | $\chi^2$ | PHB content [% dwt] $T_0$ plants Parent1 | PHB content [% dwt] $T_0$ plants Parent2 | PHB content [% dwt] $T_1$ plants Range | PHB content [% dwt] $T_1$ plants Mean | PHB content [% dwt] $T_1$ plants Median | PHB content [% dwt] $T_1$ plants SD |
|---|---|---|---|---|---|---|---|---|---|---|---|---|
| 4 | 110 | 105 | 79 | 26 | 3.0:1 | 0.01 | 0.31 | 0.39 | 0-1.24 | 0.14 | 0.06 | 0.22 |
| 5 | 78 | 74 | 53 | 21 | 2.5:1 | 0.45 | 0.15 | 0.11 | 0-0.65 | 0.15 | 0.07 | 0.16 |

We claim:

1. A transgenic switchgrass plant genetically engineered to express heterologous genes selected from the group consisting of genes encoding a PHA synthase, a thiolase and a reductase for producing polyhydroxyalkanoate to produce at least about 1% dry weight (dwt) polyhydroxyalkanoate, wherein a corresponding non-transgenic plant does not produce a specialized oil or starch storage material in excess of that needed for day-to-day metabolism.

2. The transgenic plant of claim 1 wherein the switchgrass is of a cultivar selected from the group consisting of Alamo, Blackwell, Kanlow, Nebraska 28, Pathfinder, Cave-in-Rock, Shelter and Trailblazer.

3. The transgenic plant of claim 1 wherein the transgenic plant comprises a $C_4$ NAD-malic enzyme photosynthetic pathway.

4. The transgenic plant of claim 1 wherein the transgenic plant accumulates at least 4% dry weight or greater of polyhydroxyalkanoate.

5. The transgenic plant of claim 1 wherein the polyhydroxyalkanoate comprises poly-3-hydroxybutyrate.

6. The transgenic plant of claim 1, wherein the PHA synthase is a hybrid synthase derived from *Pseudomonas oleovorans* and *Zoogloea ramigera*.

7. The transgenic plant of claim 6 wherein the thiolase and reductase are from *Ralstonia eutropha*.

8. A transgenic plant, plant part, or plant cell comprising heterologous genes selected from the group consisting of genes encoding a thiolase, a reductase, and a PHA synthase for the production of poly(hydroxyalkanoate) wherein the plant does not produce specialized oil and starch, in excess of that needed for day-to-day metabolism.

9. The transgenic plant, plant part, or plant cell of claim 8 wherein the plant also produces lignocellulosic biomass.

10. A transformed seed of the transgenic plant of claim 1.

11. A plant propagated through tissue cultures initiated from an explant from the transgenic plant of claim 1.

12. Plant feedstock comprising lignocellulosic biomass and at least about 4% dry weight of poly(hydroxyalkonate) produced from plant material from the transgenic plant of claim 1.

13. The plant feedstock of claim 12 wherein the plant is switchgrass.

14. The plant feedstock of claims 12 wherein the poly (hydroxyalkanoate) comprises poly(3-hydroxybutyrate).

15. The plant feedstock of claim 12 comprising at least 4% poly(3-hydroxybutyrate).

\* \* \* \* \*